United States Patent
Perkins et al.

(10) Patent No.: US 9,422,526 B2
(45) Date of Patent: Aug. 23, 2016

(54) ISOLATION, EXPANSION AND USE OF AUTOLOGOUS PLURIPOTENT STEM CELLS

(75) Inventors: Diana Perkins, Chapel Hill, NC (US); Clark Jeffries, Chapel Hill, NC (US); Vandana Turaga, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 254 days.

(21) Appl. No.: 14/125,910

(22) PCT Filed: Jun. 14, 2012

(86) PCT No.: PCT/US2012/042434
§ 371 (c)(1),
(2), (4) Date: Mar. 5, 2014

(87) PCT Pub. No.: WO2012/174225
PCT Pub. Date: Dec. 20, 2012

(65) Prior Publication Data
US 2014/0220682 A1    Aug. 7, 2014

Related U.S. Application Data

(60) Provisional application No. 61/496,892, filed on Jun. 14, 2011.

(51) Int. Cl.
| | | |
|---|---|---|
| C12N 5/074 | (2010.01) | |
| C12N 5/00 | (2006.01) | |
| C12N 5/0789 | (2010.01) | |
| C12N 5/0775 | (2010.01) | |

(52) U.S. Cl.
CPC ............ *C12N 5/0696* (2013.01); *C12N 5/0087* (2013.01); *C12N 5/0647* (2013.01); *C12N 5/0665* (2013.01); *C12N 2509/00* (2013.01)

(58) Field of Classification Search
None
See application file for complete search history.

(56) References Cited

U.S. PATENT DOCUMENTS

| | | | |
|---|---|---|---|
| 4,436,631 A * | 3/1984 | Graham, Jr. | B01D 11/02 210/518 |
| 6,767,738 B1 | 7/2004 | Gage et al. | |
| 2005/0189297 A1 | 9/2005 | Bosch et al. | |
| 2006/0183102 A1 | 8/2006 | Young et al. | |
| 2009/0104158 A1 | 4/2009 | Young et al. | |
| 2009/0104160 A1 | 4/2009 | Young et al. | |
| 2009/0155225 A1 | 6/2009 | Ratajczak et al. | |
| 2009/0186334 A1 | 7/2009 | Young et al. | |
| 2009/0220466 A1 | 9/2009 | Ratajczak et al. | |
| 2010/0183570 A1 | 7/2010 | Wang et al. | |
| 2010/0267107 A1 | 10/2010 | Zuba-Surma et al. | |
| 2011/0064701 A1 | 3/2011 | Young et al. | |
| 2011/0070205 A1 | 3/2011 | Crawford et al. | |
| 2011/0189136 A1 | 8/2011 | Ratajczak et al. | |
| 2012/0021482 A1 | 1/2012 | Zuba-Surma et al. | |
| 2012/0034194 A1 | 2/2012 | Wang | |
| 2012/0045758 A1 | 2/2012 | Kucia et al. | |

FOREIGN PATENT DOCUMENTS

| | | | |
|---|---|---|---|
| EP | 2 267 116 A1 | 12/2010 | |
| WO | WO9526417 A1 * | 10/1995 | ............... C12Q 1/68 |
| WO | WO 2008/148105 A1 | 12/2008 | |

OTHER PUBLICATIONS

Voullaire, Lucille, et al. "Fetal nucleated red blood cells from CVS washings: an aid to development of first trimester non-invasive prenatal diagnosis." Prenatal diagnosis 21.10 (2001): 827-834.*

Abdel-Latif et al. Evidence of mobilization of pluripotent stem cells into peripheral blood of patients with myocardial ischemia. *Exp Hematol*. Dec 2010; (epublished Aug. 2010); 38(12):1131-1142.

Bhartiya et al. Very small embryonic-like stem cells with maximum regenerative potential get discarded during cord blood banking and bone marrow processing for autologous stem cell therapy. *Stem Cells Devel*. 21(1)1-6 (prepublished online Jul. 22, 2011).

Dawn et al. Transplantation of bone marrow-derived very small embryonic-like stem cells attenuates left ventricular dysfunction and remodeling after myocardial infarction. *Stem Cells*. Jun. 2008;26(6):1646-1655.

Drukala et al. Stem Cells, Including a Population of Very Small Embryonic-Like Stem Cells, are Mobilized Into Peripheral Blood in Patients After Skin Burn Injury. *Stem Cell Rev*. Mar. 2012, 8(1):184-194.

Huang et al. Bone marrow transplantation temporarily improves pancreatic function in streptozotocin-induced diabetes: potential involvement of very small embryonic-like cells. *Transplantation*. Mar. 27, 2010;89(6):677-685.

Ito et al. A new continuous-flow cell separation method based on cell density: principle, apparatus, and preliminary application to separation of human buffy coat. *J Clin Apher*. 2001; 16(4):186-191.

Kucia et al. A population of very small embryonic-like (VSEL) CXCR4(+)SSEA-1(+)Oct-4+ stem cells identified in adult bone marrow. *Leukemia*. May 2006;20(5):857-869.

Kucia et al. Bone marrow-derived very small embryonic-like stem cells: their developmental origin and biological significance. *Dev Dyn*. Dec. 2007; 236(12):3309-3320.

Kucia et al. Morphological and molecular characterization of novel population of CXCR4+ SSEA-4+ Oct-4+ very small embryonic-like cells purified from human cord blood: preliminary report. *Leukemia*. Feb. 2007; 21(2):297-303.

Liu et al. Identification of small Sca-1(+), Lin(-), CD45(-) multipotential cells in the neonatal murine retina. *Exp Hematol*. Sep. 2009;37(9):1096-1107, 1107 e1091.

(Continued)

*Primary Examiner* — Robert Yamasaki
(74) *Attorney, Agent, or Firm* — Myers Bigel & Sibley, P.A.

(57) ABSTRACT

The present invention relates to methods of isolating and culturing autologous pluripotent stem (aPS) cells. The present invention also provides isolated aPS cells, populations of aPS cells and cultures of aPS cells. Further provided are culture media for expanding aPS cells and methods of culturing aPS cells. The invention also provides for the use of aPS cells, e.g., for diagnostics, drug evaluation and screening, and regenerative medicine.

14 Claims, 11 Drawing Sheets

(56) References Cited

OTHER PUBLICATIONS

Machalinski et al. Mobilization of human hematopoietic stem/progenitor-enriched CD34+ cells into peripheral blood during stress related to ischemic stroke. *Folia Histochem Cytobiol.* 2006;44(2):97-101.
McGuckin et al. *Nature Protocols* 2008; 3(6):1046-1055.
McGuckin et al. Culture of embryonic-like stem cells from human umbilical cord blood and onward differentiation to neural cells in vitro. *Nat Protoc.* 2008;3(6):1046-1055.
McGuckin et al. Embryonic-like stem cells from umbilical cord blood and potential for neural modeling. *Acta Neurobiol Exp (Wars).* 2006;66(4):321-329.
McGuckin et al. Umbilical cord blood stem cells can expand hematopoietic and neuroglial progenitors in vitro. *Exp Cell Res.* 2004;295(2):350-359.
Paczkowska et al. Clinical evidence that very small embryonic-like stem cells are mobilized into peripheral blood in patients after stroke. *Stroke.* Apr. 2009;40(4):1237-1244.
Parte et al. Detection, Characterization, and Spontaneous Differentiation In Vitro of Very Small Embryonic-Like Putative Stem Cells in Adult Mammalian Ovary. *Stem Cells Dev.* 20(8): 1451-1464 (Published online Feb. 3, 2011).
Perkins et al. Improved Methods to isolate and culture VSEL stem cells from humans. ISSCR 9th Annual Meeting, Jun. 15-18, 2011, Toronto Ontario (Poster and Abstract).
Perkins et al. microRNA expression in the prefrontal cortex of individuals with schizophrenia and schizoaffective disorder. *Genome Biology* 2007; 8(2):R27.
Ratajczak et al. A multi-instrumental approach to identify and purify very small embryonic like stem cells (VSELs) from adult tissues. *Micron.* 2009;40(3):386-393.
Ratajczak et al. Adult murine bone marrow-derived very small embryonic-like stem cells differentiate into the hematopoietic lineage after coculture over OP9 stromal cells. *Exp Hematol.* Feb. 2011; 39(2):225-237.
Ratajczak et al. *Cell. Ther. Transplant.* 2008; 99 Pages.
Ratajczak et al. Hematopoietic differentiation of umbilical cord blood-derived very small embryonic/epiblast-like stem cells. *Leukemia.* Aug. 2011 25(8):1278-1285.
Ratajczak et al. Stem cells for neural regeneration—a potential application of very small embryonic-like stem cells. *J Physiol Pharmacol.* Feb. 2011; 62(1):3-12.
Ratajczak et al. Very small embryonic-like (VSEL) stem cells: purification from adult organs, characterization, and biological significance. *Stem Cell Rev.* 2008;4(2):89-99.
Sovalat et al. Identification and isolation from either adult human bone marrow or G-CSF-mobilized peripheral blood of CD34(+)/CD133(+)/CXCR4(+)/ Lin(-)CD45(-) cells, featuring morphological, molecular, and phenotypic characteristics of very small embryonic-like (VSEL) stem cells. *Exp Hematol.* 2011;39(4):495-505.
Tong et al. A novel high throughput immunomagnetic cell sorting system for potential clinical scale depletion of T cells for allogeneic stem cell transplantation. *Exp Hematol.* 2007; 35(10):1613-1622.
Wlodkowic et al. Tumors on chips: oncology meets microfluidics. *Curr Opin Chem Biol.* 2010; 14(5):556-567.
Wojakowski et al. Circulating very small embryonic-like stem cells in cardiovascular disease. *J Cardiovasc Transl Res.* Apr. 2011; 4(2):138-144.
Wojakowski et al. Mobilization of bone marrow-derived Oct-4+ SSEA-4+ very small embryonic-like stem cells in patients with acute myocardial infarction. *J Am Coll Cardiol.* Jan. 6, 2009;53(1):1-9.
Wojakowski et al. Mobilization of CD34(+), CD117(+), CXCR4(+), c-met(+) stem cells is correlated with left ventricular ejection fraction and plasma NT-proBNP levels in patients with acute myocardial infarction. *Eur Heart J.* Feb. 2006;27(3):283-289.
Zuba-Surma et al. Bone marrow-derived pluripotent very small embryonic-like stem cells (VSELs) are mobilized after acute myocardial infarction. *J Mol Cell Cardiol.* May 2008;44(5):865-873.
Zuba-Surma et al. *J. Cell. Mol. Med.* 2008; 12(1):292-303.
Zuba-Surma et al. Optimization of isolation and further characterization of umbilical-cord-blood-derived very small embryonic/epiblast-like stem cells (VSELs). *Eur J Haematol.* 2010; 84(1):34-46.
Zuba-Surma et al. Transplantation of expanded bone marrow-derived very small embryonic-like stem cells (VSEL-SCs) improves left ventricular function and remodeling after myocardial infarction. *J Cell Mol Med.* Jun. 2011, 15(6):1319-1328.
Zuba-Surma et al. Very small embryonic-like stem cells are present in adult murine organs: ImageStream-based morphological analysis and distribution studies. *Cytometry A.* Dec. 2008; 73A(12):1116-1127.
Notification Concerning Transmittal of International Preliminary Report on Patentability in corresponding PCT Application No. PCT/US2012/042434, mailed Jan. 3, 2014 (8 pages).
International Search Report and Written Opinion issued in corresponding PCT Application No. PCT/US2012/042434, mailed Jan. 25, 2013 (12 pages).
Reddy et al. "Isolation of Stem Cells from Human Umbilical Cord Blood", *Methods Mol. Biol* 407:149-163 (2007).
Van Beem et al. "Recovery and functional activity of monocuclear bone marrow and peripheral blood cells after different cell isolation protocols used in clinical trials for cell therapy after acute myocardial infarction", *EuroIntervention* 4:133-138 (2008).
Hasan et al. Isolation of Human Blood Progenitor and Stem Cells from Peripheral Blood by Magnetic Bead:, *bio-protocol* 2(21) (2012).

\* cited by examiner

| SOURCE | DENSITY (g/mL) |
|---|---|
| THROMBOCYTES | 1.04-1.06 |
| LYMPHOCYTES | 1.06-1.08 |
| GRANULOCYTES | 1.08-1.09 |
| ERYTHROCYTES | 1.09-1.10 |

*FIG. 1*

| CELL | MEASURE 1 | MEASURE 2 | MEASURE 3 | AVERAGE |
|---|---|---|---|---|
| 1 | 1.05 | 1.2 | 1.17 | 1.14 |
| 2 | 1.44 | 1.39 | 1.46 | 1.43 |
| 3 | 1.11 | 1.2 | 1.26 | 1.19 |

| CELL | MEASURE 1 | MEASURE 2 | MEASURE 3 | AVERAGE |
|---|---|---|---|---|
| 1 | 1.05 | 1.2 | 1.17 | 1.14 |
| 2 | 1.44 | 1.39 | 1.46 | 1.43 |
| 3 | 1.11 | 1.2 | 1.26 | 1.19 |
| 4 | 2.1 | 1.93 | 2.01 | 2.01 |
| 5 | 1.72 | 1.62 | 1.4 | 1.58 |
| 6 | 1.09 | 1.11 | 1.06 | 1.09 |
| 7 | 2 | 1.97 | 1.83 | 1.93 |
| 8 | 1.87 | 2.01 | 1.79 | 1.89 |
| 9 | 0.81 | 0.93 | 0.89 | 0.88 |
| 10 | 1.31 | 1.39 | 1.36 | 1.35 |
| 11 | 2.13 | 2.2 | 2.2 | 2.18 |
| 12 | 1.63 | 1.7 | 1.74 | 1.69 |
| 13 | 2.57 | 2.47 | 2.43 | 2.49 |
| 14 | 1.27 | 1.14 | 1.19 | 1.20 |
| 15 | 1.08 | 1.34 | 1.39 | 1.27 |
| 16 | 1.69 | 1.65 | 1.74 | 1.69 |
| 17 | 2.17 | 1.93 | 1.98 | 2.03 |
| 18 | 1.21 | 1.16 | 1.26 | 1.21 |
| 19 | 3.15 | 3.13 | 3.58 | 3.29 |
| 20 | 1.87 | 1.86 | 1.61 | 1.78 |
| 21 | 0.99 | 1.06 | 1 | 1.02 |
| 22 | 1.49 | 1.54 | 1.5 | 1.51 |
| 23 | 0.97 | 1.03 | 1.08 | 1.03 |
| 24 | 1.21 | 1.3 | 1.4 | 1.30 |
| 25 | 1.04 | 0.99 | 1.1 | 1.04 |
| 26 | 3.55 | 3.66 | 3.44 | 3.55 |
| 27 | 0.99 | 1 | 1.01 | 1.00 |
| | | | MEAN | 1.62 |
| | | | SD | 0.66 |

| SUBJECT | AVERAGE NUMBER OF CELLS IN 6.25 nL SQUARE | HEMOCYTO-METER COUNT, AVERAGE CELLS IN A "GREEN" SQUARE/nL | TOTAL NUMBER OF aPS CELLS ISOLATED FROM 10 mL OF WHOLE BLOOD AS CALCULATED FROM HEMOCYTO-METER | TOTAL NUMBER OF aPS CELLS (Q1&Q2) ISOLATED FROM 10mL OF WHOLE BLOOD AS CALCULATED BY FLOW CYTOMETRY USING COUNTING BEADS (Q4) |
|---|---|---|---|---|
| A | | | | 110,860 |
| B | | | | 104,860 |
| C | | | | 108,390 |
| D | 10 | 1.6 | 112,000 | |
| E | 12 | 1.9 | 134,400 | |
| F | 20 | 3.2 | 224,000 | |

FIG. 4

ISOLATION, EXPANSION AND USE OF AUTOLOGOUS PLURIPOTENT STEM CELLS

RELATED APPLICATION INFORMATION

This application claims the benefit of U.S. Provisional Application No. 61/496,892, filed Jun. 14, 2011, the disclosure of which is incorporated by reference herein in its entirety.

FIELD OF THE INVENTION

The present invention relates to methods of isolating and culturing autologous pluripotent stem (aPS) cells as well as isolated aPS cells and populations of aPS cells and cultures of aPS cells.

BACKGROUND OF THE INVENTION

Stem cells derived from an animal are potentially useful for a variety purposes, including regeneration of damaged tissues, reproduction, and as cellular models that could inform personal medicine, including diagnoses, treatments to alleviate a condition of disease or disorder, or warnings of adverse reaction to a potential treatment. Currently, induced pluripotent stem cells (iPS cells) are the dominant model system. iPS cells are derived from dividing multipotent or committed cells (such as fibroblasts, fat stem cells, lymphocytes) by the introduction of different combinations of specific transcription factors involved in regulating pluripotency (for example, OCT4, SOX2, NANOG, KLF4, MYC, LIN28, TERT). The transcription factor levels are increased by a variety of mechanisms, including viral reprogramming of the cells' DNA, and the direct introduction into the cell or pluripotency proteins or of mRNA encoding for the pluripotency proteins. The iPS cells generated through these methods are extraordinarily similar to embryonic stem cells (ES cells), including the capacity to differentiate into cells from all three germ layers, gene expression profiles, and capacity to form teratomas when injected into animals. The iPS cells offer the advantage over ES cells of being from the organism of interest, that is, they are autologous. However, obstacles to clinical use of iPS cells include that iPS cells may be prone to cancer or other pathologies, that the iPS cells, as "artificial", may not faithfully recapitulate disease processes (e.g., due to epigenetic factors), and that generation of iPS cells is relatively expensive and time consuming. Thus, there is a need in the art for methods to identify and directly harvest autologous pluripotent stem (aPS) cells that reduce or avoid the aforementioned limitations, from an organism. The pluripotent stem cells that an organism harbors from birth into adulthood presumably serve tissue regeneration in that organism, and as such would not generate teratomas or cancers when re-injected back into the organism; they might also have the capacity to recapitulate the developmental program of that organism during differentiation. Reliable methods to isolate relatively pure populations of pluripotent stem cells from an organism at low cost and to culture these cells outside of the organism are required before the promise of pluripotent stem cells can be achieved.

Currently, stem cells are isolated from peripheral blood or other tissues using a variety of methods. Several methods require labeled antibodies as a core feature, including fluorescent activated cell sorting (FACS) and immunomagnetic separation methods[1-3]. Other methods used to isolate stem cells from an organism include selecting the cells based on expression of a specific cell marker or markers associated with pluripotency. For example, cells can be sorted on the basis of expression of a specific cell marker or markers using flow cytometry or magnets, depending on the characteristics of the antibody used to identify the marker. Disadvantages of these methods include that the methods use expensive technologies and may take an unrealistic amount of time (for example days) to isolate sufficient cells for clinical use[3].

Some methods of stem cell isolation include centrifugation of a cell suspension or lysate over density barrier; in all reports of these methods the density of the barrier is less than or equal to 1.085 g/mL[4]. Other methods depend on culture selection, as stem cells are long-lived and will thus survive after other, contaminating cell types have died[5,6]. Regarding isolation from blood, red blood cells may be removed as a first step, for example with chemical lysis[7] or with a PERCOLL™ barrier[8].

Accordingly, there is a need in the art for populations of autologous stem cells as well as improved methods and culture media for isolating and culturing pluripotent stem cells.

SUMMARY OF THE INVENTION

Autologous pluripotent stem (aPS) cells are proposed to be primitive stem cells in the postnatal animal and to play a role in tissue regeneration. aPS cells have been isolated from human peripheral blood and cerebrospinal fluid, and are proposed to exist in other and in animal tissues. These cells exhibit phenotypic similarity to embryonic stein cells and induced pluripotent stem (iPS) cells, including their protein and RNA expression (e.g., OCT4 (POU5F1), NANOG, SSEA4, TRA-1-60, TRA-1-80), and their high nuclear to cytoplasm ratio. However, as compared with ESC and iPS cells, the aPS cell size is smaller, generally from about one to about three microns, and by virtue of the small size, the nucleus contains densely packed heterochromatin. The nucleus of aPS cells has been observed to stain with DNA specific (e.g. DRAQ5™) and non-specific (e.g. 4',6-diamidino-2-phenylindole [DAPI]) nucleic acid stains. In general, aPS cells have a density that is typically greater than 1.1 g/mL, a density greater than that of most other cells, including red blood cells. APS cells also differ from iPS cells in that do they generally do not form teratomas, and thus may have a low risk of cancer with regenerative medication applications.

The present invention is based, in part, on the discovery that aPS cells possess a high specific gravity relative to other cells, which can be exploited to isolate aPS cells. APS cells are smaller and denser than previously identified stem cell populations and can be isolated and distinguished from previously identified stem cell populations using these characteristics. The isolation methods of the invention improve on conventional methods of stein cell isolation by: (1) optimizing the number of aPS stem cells recovered per mL of whole blood, (2) using relatively simple technologies, making the methods less costly to implement and potentially usable in settings where FACS sorting of cells is not currently available; and/or (3) simplifying procedures to a protocol that in some embodiments can take as little as 2 to 6 hours and that is easily scalable so that aPS cells can be isolated from relatively large amounts of blood (e.g., a pint of blood or more), other animal body fluids or tissues, or other cell mixtures.

Previous methods for isolating stem cells often involve centrifugation steps, for example, to remove red blood cells or to pellet the cells after antibody labeling. Centrifugation parameters are typically set by a trial and error process, and by convention are generally between 300-600 g and 5-30 minutes, although different parameters may be specified. Height of the cell suspension is generally set by convenience. It is pertinent to note that the rotational speed is often given in rpms, rather than the g-force, although the g-force generated by a given rotational speed depends on the radius of the centrifuge rotor. The height of the cell suspension to be centrifuged is rarely, if ever, specified, nor is the viscosity of the liquid. For example, in the detailed report by McGuckin and colleagues[9], in step 6 (removal of red blood cells) they specify centrifugation of the initial umbilical cord blood at 400 g for 30 minutes. Assuming a cell suspension height of 15 cm (as shown in FIG. 1 of the paper), using these parameters would lead to loss of ~50% of the aPS cells, as the aPS cells would enter the PERCOLL™ and accumulate in a pellet, to be discarded along with the PERCOLL™ or with the red blood cells.

As one aspect, the present invention provides methods for isolating a very small (e.g., 1 to 5 micron diameter), primitive stem cell expressing OCT4 in the nucleus from a biological sample such as an animal body fluid (including blood, plasma, serum, bone marrow, lymph, tears, urine, breast milk, seminal fluid, saliva, amniotic fluid, bronchial lavage, cerebrospinal fluid, pleural fluid, peritoneal fluid and/or colostrum) and/or animal tissue (including, but not limited to brain and/or olfactory epithelium). In representative embodiments, the cell separation method is based on cell density. In embodiments, the method includes use of Stokes' Equation to determine optimal centrifugation parameters, which may minimize cell loss, avoid insufficient centrifugation time that could result in contamination of the final aPS cell product with other cell types, and avoid excessive centrifugation speeds and time that may damage cells and/or result in low yields of aPS cells. In representative embodiments, the method includes using a density barrier, continuous flow cell separation, and/or other methods that separate cells based on specific gravity.

An alternative embodiment for cell separation uses an immunomagnetic separation method[28] such as the Quadrasep QMC™ quadrapole magnetic sorter (Ikotech). Regarding blood processing, a representative embodiment uses negative depletion to remove contaminating platelets, white blood cells and/or red blood cells. Negative selection can also be accomplished using a microfluidics platforms and antibody labeled microposts such as the CTC-Chip[29]. Another alternative embodiment uses positive selection with immunopurification by labeling of cells for immunomagnetic separation[28] and/or a microfluidics platform.

The present invention also provides culture media and methods of culturing aPS cells using a cell culture system suitable for their expansion and/or long-term survival.

The invention further provides methods of using aPS cells or their derivatives (e.g., taken from an individual patient) to evaluate the safety and/or effectiveness of a compound (e.g., a pharmaceutical agent) or other therapies for the prevention and/or treatment of an illness, to determine disease mechanism, and/or to diagnose disease on an individualized basis. In addition, the invention provides methods of using aPS cells, differentiated aPS cells, genetically modified aPS cells, or other aPS cell derivatives for the purpose of screening a compound (e.g., a small molecule pharmaceutical) for evaluation of safety and/or effectiveness. In representative embodiments, the method is a high through-put screening method employing many clones of an aPS cell culture. In some embodiments, the aPS cells or their derivatives represent a patient population or sub-population. In other embodiments, aPS cells can also be used in vivo for regenerative medicine.

Accordingly, as one aspect, the invention provides a method for isolating autologous pluripotent stem (aPS) cells from a mixture of animal cells, the method comprising:

(a) centrifuging the mixture of animal cells over a density barrier medium having a specific gravity of at least 1.09, such that a fraction containing the aPS cells migrates into the density barrier medium and to a position within and/or below the density barrier; and (b) collecting the fraction within and/or below the density barrier medium containing the aPS cells.

In embodiments of the invention, centrifuging the mixture of animal cells in (a) comprises centrifuging the mixture of animal cells over a density barrier medium within an inner centrifuge tube, wherein the inner centrifuge tube comprises an opening formed in a bottom portion thereof and is positioned in an outer centrifuge tube, such that the density barrier medium is in communication between the inner and outer centrifuge tubes, and wherein there is a space between the bottom of the inner centrifuge tube and the bottom of the outer centrifuge tube, and wherein the inner centrifuge tube is enclosed; and wherein the mixture of animal cells is centrifuged such that the fraction containing the aPS cells migrates out of the inner centrifuge tube through the opening formed in the bottom portion thereof and into the density barrier medium to a position within and/or below the density barrier medium in the outer centrifuge tube.

The invention further provides an aPS cell isolated according to a method of the invention.

Further provided is an isolated population of aPS cells from an animal subject having a mean diameter in the range of 1 to 4 microns.

Still further, the invention provides an isolated population of aPS cells from an animal subject that has been continuously cultured for at least one month and expresses POU5F1 (OCT4).

As another aspect, the invention provides a culture medium for expanding aPS cells, wherein the culture medium comprises:

(a) one or more mitogenic factors;
(b) one or more cell survival factors;
(c) selenium; and
(d) a simple sugar.

In embodiments, the culture medium does not comprise serum and/or plasma.

In embodiments, the one or more mitogenic factors comprise epidermal growth factor, transformed growth factor-α, Nodal, Noggin, leukocyte inhibitory factor, Activin A, stem cell factor, heregulin, hepatocyte growth factor, platelet derived growth factor, and/or fibroblast growth factor-2.

In embodiments, the cell survival factor comprises transferrin, platelet-derived growth factor, insulin-like growth factor 1 and/or insulin-like growth factor 2.

In embodiments, the culture medium comprises: (i) epidermal growth factor; (ii) fibroblast growth factor-2; (iii) glucose; (iv) putrescine; (v) progesterone; (vi) selenium; (vii) insulin; (viii) transferrin; and (ix) ascorbic acid.

In embodiments, the culture medium comprises: (i) platelet derived growth factor and/or fibroblast growth factor-2; (ii) glucose; (iii) selenium; (iv) insulin; and (v) transferrin.

As another aspect, the invention provides a method of culturing aPS cells, the method comprising culturing a population of aPS cells in a culture vessel containing a culture medium of the invention.

As yet another aspect, the invention provides the use of an isolated aPS cell to evaluate safety of a compound and/or effectiveness of a compound for treatment of disease.

Still further, the invention provides for the use of an isolated aPS cell to evaluate the mechanism underlying a disease or disorder to yield an individualized diagnosis in an animal subject from which the aPS cell was isolated.

As another aspect, the invention provides for the use of an isolated aPS cell to identify a candidate compound of interest.

Still further, the invention provides for the use of a aPS cell or a population or culture of aPS cells isolated and/or cultured according to the present invention for use in biobanking cells for future use.

As yet another aspect of the invention provides for use of an aPS cell or a population or culture of aPS cells for development of germ cells and assisted reproduction.

Still further, the invention provides for the use of an aPS cell or a population or culture of aPS cells isolated and/or cultured according to the present invention for use in regenerative medicine.

These and other aspects of the invention are described in more detail in the following description of the invention.

BRIEF DESCRIPTION OF THE DRAWINGS

FIG. 1. Specific gravity of cells found in the peripheral blood. Taken from www.gelifesciences.com/aptrix/upp01077.nsf/Content/cellpreparation_home~products_cell~density_gradient media~percoll?opendocument&moduleid=167165&cmpid=p pc000037 on Jun. 2, 2011.

FIG. 4. Number of cells isolated from peripheral blood as determined using two different methods.

DETAILED DESCRIPTION OF THE INVENTION

Figure 2:
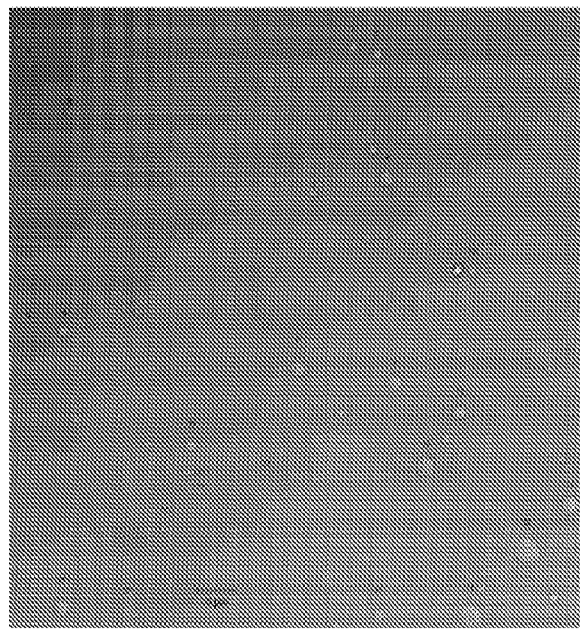
FIG. 2. aPS cells were isolated from 10 mL of whole blood from a healthy male with a density based method as described in Example 1 herein. Cells were fixed with 4% formaldehyde, stained with OCT4 marker (blue fluorescence), washed, and then suspended in 70 μL of PBS. A 7 μL drop was plated on IMMUNOSELECT® Adhesion slides (Mo Bi Tec) and the slide placed in a moist chamber overnight to allow cells to adhere. The cells were gently washed with PBS, and then mounted with Fluoro-Gel mounting medium (Electron Microscopy Sciences). A sealant (nail polish) was used to hold the cover slip in place. Images were obtained using a Zeiss 510 Laser Scanning Confocal Microscope at 63× with oil microscopy by Dr. Neil Kramarcy of the University of North Carolina Michael Hooker Microscopy Facility. DIC and fluorescent images are merged.

The present invention provides methods to isolate aPS cells from a mixture of animal cells (e.g., a biological sample comprising an animal body fluid and/or animal tissue), methods to culture and expand aPS cells (e.g., over long periods of time, for example, at least about 1, 2, 3 or 4 months) without substantial differentiation, and use of aPS cells for in vitro investigations of disease cause and treatment as well as in vivo uses in regenerative medicine.

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete to fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

As used in the description of the invention and the appended claims, the singular forms "a," "an" and "the" are intended to include the plural forms as well, unless the context clearly indicates otherwise.

The term "about," as used herein when referring to a measurable value such as a dosage, time, temperature, and the like, is meant to encompass variations of ±20%, ±10%, ±5%; ±1%, ±0.5%, or even ±0.1% of the specified amount.

Numerical ranges as described herein are intended to be inclusive unless the context indicates otherwise. For example, the numerical range of "1 to 10" or "1-10" is intended to be inclusive of the values 1 and 10.

Also as used herein, "and/or" refers to and encompasses any and all possible combinations of one or more of the associated listed items, as well as the lack of combinations when interpreted in the alternative ("or").

The features of the invention described herein can be used in any combination. Moreover, the present invention also contemplates that in some embodiments of the invention, any feature or combination of features set forth herein can be excluded or omitted.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

By "consisting essentially of" as used herein, it is meant that the indicated compound, composition, formulation and the like does not include any other material elements (i.e., elements that materially impact the structure and/or function of the method, compound, composition or formulation).

As used herein, a "biological fluid" is generally from an animal subject and can be any biological fluid that can be used for the isolation of aPS cells including without limitation: blood (e.g., peripheral blood and/or cord blood), plasma, serum, bone marrow, lymph, tears, urine, breast milk, seminal fluid, saliva, amniotic fluid, bronchial lavage, cerebrospinal fluid, pleural fluid, peritoneal fluid, colostrum and/or any other biological fluid.

The term "biological tissue" or "tissue" as used herein is generally a tissue from an animal subject and includes, without limitation, neural tissue (e.g., brain, eyes), liver, kidney, fat, skeletal muscle, heart, placenta, spleen, stomach, small intestine, colon, rectum, lung, pancreas, epithelium (e.g., olfactory epithelium), reproductive tissue (e.g., testis, ovary, uterus, vagina, cervix and/or fallopian tube), bone marrow, dental pulp, gum, hair follicle, nail bed, blood vessel, connective tissue, skin, umbilical cord, an embryo and/or any other tissue type. Tissues can be from postnatal (e.g., adult), neonatal and/or embryonic subjects.

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the onset of at least one clinical symptom, relapse and/or progression of the disease or disorder.

The terms "prevent," "preventing" and "prevention" (and grammatical variations thereof) refer to avoidance, prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the methods of the present invention.

An "effective" amount as used herein is an amount sufficient to achieve a desired outcome, and is optionally a treatment effective amount.

A "treatment effective" amount as used herein is an amount that is sufficient to treat (as defined herein) the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptom in a subject and/or to reduce and/or delay the severity of the onset of a disease, disorder and/or clinical symptom in a subject relative to what would occur in the absence of the methods of the invention. Those skilled in the art will appreciate that the level of prevention need not be complete, as long as some benefit is provided to the subject.

As used herein, the terms "increase," "increases," "increased" and "increasing" as well as "enhance," "enhances," "enhanced," "enhancing," and "enhancement" and similar terms, indicates an elevation in the specified parameter, for example, an elevation of at least about 10%, 20%, 30%, 40%, 50%, 2-fold, 3-fold, 4-fold, 5-fold, 10-fold, 15-fold, 20-fold or more.

As used herein, the terms "reduce," "reduces," "reduced," "reducing," "reduction" as well as "impair," "impairs," "impaired," "impairing," "impairment" and similar terms indicate a decrease in the specified parameter, e.g., of at least about 10%, 20%, 30%, 40%, 50%, 60%, 75%, 80%, 85%, 90%, 95%, 97% or more. In particular embodiments, the reduction or impairment results in no or essentially no (i.e., an insignificant amount, for example, less than about 10% or even 5%) detectable amount or activity.

A "mixture of animal cells" (and similar terms) as used herein refers to a plurality of cells comprised of two or more cell types, or suspected to comprise two or more cell types (e.g., aPS cells and non-aPS cells, such as red blood cells). In general, the mixture of animal cells comprises, or is believed to comprise, one or more aPS cells. In representative embodiments, the mixture of animal cells comprises a biological sample. In other representative embodiments, the mixture of animal cells comprises cultured cells.

The term "animal" as used herein includes both avians and mammals, mammals including but not limited to humans, non-human primates (e.g., monkeys, baboons, and chimpanzees), dogs, cats, goats, horses, pigs, cattle, sheep, and the like, and laboratory animals (e.g., rats, mice, gerbils, hamsters, and the like). Avians include chickens, ducks, turkeys, geese, quails and birds kept as pets (e.g., parakeets, parrots, macaws, and the like). Suitable animals include both males and females and animals of all ages including infant, neonatal, juvenile, adolescent, adult and geriatric animals as well as embryos. In representative embodiments, the animal is not an embryo.

As used herein, an "aPS cell" is a small stem cell with a diameter in the range of about 0.5 or 1 micron to about 2, 2.5, 3, 4, 5 or 6 microns, a relatively high density as described further herein, and expression of one or more pluripotency genes associated with stemness, as also described further herein (e.g., expression of OCT4 in the nucleus and/or SSEA4 on the cell surface or the homologous genes in non-human animals). In embodiments of the invention, the aPS cell has one or more characteristics selected from: tightly packed heterochromatin, a nucleus that stains with DNA specific (e.g., DRAQ5™) and/or non-specific (e.g., DAPI) nucleic acid stains, exclusion of trypan blue (i.e., trypan blue negative) and/or utilization of glucose as a carbon source. In further representative embodiments, the aPS cell is adherent in culture. In some embodiments, the aPS cell is pluripotent. In embodiments of the invention, the aPS cell is capable of differentiation into cells of endoderm, mesoderm, and ectoderm, as well as into germ cells.

An "isolated" cell refers to a cell that is at least partially separated from other components and/or cells with which it is normally associated in its natural state. In representative embodiments, the "isolated" cell is at least about 50%, 60%, 70%, 80%, 90%, 95%, 96%, or 97% or more pure.

aPS Cell Isolation

The invention provides methods for isolating aPS cells. In representative embodiments, the method utilizes density centrifugation or any other protocol that can separate cells on the basis of density (specific gravity). As another example, a continuous flow cell separation method[30] may also be used that is based on cell density.

In embodiments, the invention provides a method for isolating aPS cells from a mixture of animal cells, the method comprising: (a) centrifuging the mixture of animal cells over a density barrier medium, such that a fraction containing the aPS cells migrates or travels into the density barrier medium (e.g., migrates or travels downward) to a position within and/or below the density barrier medium (e.g., into the density barrier medium, and optionally through the barrier to a position below the density barrier medium); and (b) collecting the fraction within and/or below the density barrier medium containing the aPS cells. Optionally, the method can further comprise culturing the cells of (b) and/or evaluating the cells of (b), for example, by counting the aPS cells, determining their size and/or confirming the presence of markers characteristic of aPS cells (e.g. OCT4 in the nucleus and/or SSEA4 on the cell surface or the homologous proteins in non-human animals). Optionally, aPS cells migrate below the density barrier medium and form a pellet (e.g., the fraction comprising the aPS cells comprises or consists of a pellet).

In embodiments of the invention, the density centrifugation is carried out at a predetermined centrifugal force and/or time. In representative embodiments, the cell mixture is centrifuged over the density barrier medium at a centrifugation speed and duration calculated using Stokes' Equation. In particular embodiments, all centrifugation steps in the isolation method are carried out according to Stokes' Equation.

Stokes' Equation calculates the terminal velocity of a particle given the centrifugal force, particle diameter, particle density, and density and viscosity of the medium in which the particle is suspended. Since terminal velocity is obtained (almost) instantaneously, Stokes' Equation can be used to calculate the centrifugation time for any particle (including an aPS cell) to migrate into the density barrier medium and/or through the density barrier medium to a position below the density barrier medium (optionally to form a pellet), including aPS cells.

aPS cells isolated according to embodiments of the invention generally have a specific gravity greater than about 1.05, 1.06, 1.07, 1.08, 1.09, 1.1, 1.11, 1.12, 1.13 or 1.14. In representative embodiments, the aPS cells isolated according to the present invention have a specific gravity greater than about 1.09, 1.1, 1.11, 1.12, 1.13 or 1.14. The specific gravity of various human cells is given in Table 1. Note that the density of other cells in the peripheral blood, including lymphocytes, granulocytes, and erythrocytes is almost exclusively less than 1.1 g/mL, e.g., in a solution with osmolarity similar to bodily fluids.

In addition, aPS cells isolated according to representative embodiments of the invention have a diameter ranging from about 0.5 or 1 microns to about 2, 2.5, 3, 4, 5 or 6 microns (see FIG. 1). In embodiments of the invention, to calculate centrifugation parameters according to Stokes' Equation, it is assumed that aPS cells have a minimum diameter of 1 micron and a minimum specific gravity in the range of 1.1 to 1.14. Those skilled in the art will appreciate that a lower or greater specific gravity value and/or smaller or larger diameter value can be used when calculating centrifugation parameters, noting that efficiency of isolation may be impacted. For example, the diameter can be assumed to be about 0.5, 0.75, 1, 1.25, 1.5, 1.75, 2, 2.25, 2.5, 2.75, 3, 3.25, 3.5, 3.75, 4, 4.25, 4.5, 4.75 or 5 microns, or any other value therebetween or a lower or greater value. Likewise, the specific gravity can be assumed to be about 1, 1.01, 1.02, 1.03, 1.04, 1.05, 1.06, 1.07, 1.08, 1.09, 1.1, 1.105, 1.11, 1.115, 1.12, 1.125, 1.13, 1.135 or 1.14 or any other value therebetween or a lower or greater value for the purposes of determining centrifugation force and time.

In embodiments of the invention, the use of information on the size range of aPS cells, the density of the aPS cells, the density and viscosity of the fluid in which the aPS cells are suspended, the density and viscosity of the density barrier medium, and the height of the fluid in the centrifugation vessel (e.g., centrifugation tube) is used to determine the centrifugation force and time to achieve migration of aPS cells of desired sizes and specific gravities into the density barrier medium and/or to a position below the density barrier medium, e.g., by using Stokes' Equation.

$$V_t = gd^2(p_p - p_m)/k\mu, \text{ and } T = h/V_t \quad \text{Stokes' Equation:}$$

where:
$V_t$ is the terminal velocity of the particle, in units of distance per unit time
g is the gravitational force (set by the user)
d is the diameter of the particle
$p_p$ is the density of the particle
$p_m$ is the density of the medium
$\mu$ is the viscosity of the medium
T is the centrifugation time (determined by the equation and then set by the user)
h is the height of cell suspension to be centrifuged (height of fluid in a centrifuge tube)
k is a constant, dimensionless number determined by the units selected for the physical parameters. In one embodiment, the units of the parameters can be g in m/s$^2$, $V_t$ in m/s, d in m, $p_p$ in g/mL, $p_m$ in g/mL, $\mu$ in Ns/(m$^2$), and h in m. Such choices of units leads to a value for k of 0.018.

Representative values for the above parameters are g=9.8 m/s², d=2⁻⁶ m, $p_p$=1.2, $p_m$=1.1, and μ=0.001 Ns/m².

Thus, in representative density centrifugation methods according to the invention, gravitational force and centrifugation time can be selected using Stokes' Equation based on the assumption that aPS cells have a specific gravity of 1.1 and a diameter of 1 micron and taking into account the height of the suspension fluid. The contamination of the aPS cell fraction with other cells, and the proportion of aPS cells isolated, depends in part on the specified parameters and the skill of the practitioner to prevent contamination from the cells that accumulate upon centrifugation above the density barrier. Thus, other values can be selected for specific gravity and diameter as described herein.

In embodiments, the distance from the top of the cell suspension to the top of the density barrier material and density of the cell suspension fluid (usually similar to water), distance from the top of the density barrier material to the opening of the inner tube and viscosity of the density barrier material (often, but not always about 10-fold more viscous than water), as well as assumed minimum diameter and density of cell can be used according to Stokes' Equation to determine the centrifugation time at a preferred g-force.

In one embodiment Stokes' Equation is programmed into a spreadsheet or other application, such that the user may conveniently enter physical parameters to calculate centrifugation time. Alternatively, the user may algebraically invert the equations to calculate, for example, g-force required for a combination of desired sample fluid height h and a desired centrifugation time T.

In embodiments of the invention, the cell mixture is centrifuged over the density barrier medium at a centrifugation force of at least about 100 g. In embodiments, the centrifugal force is at least about 100 g, 200 g, 300 g, 400 g, 500 g, 600 g, 700 g, 800 g, 900 g or 1000 g and/or is less than about 10,000 g, 5000 g, 4000 g, 3000 g, 2000 g, 1500 g, 1200 g or 1000 g (encompassing any combination of values as long as the lower value is less than the upper value). In embodiments of the invention, the centrifugal force is about 800 g to 1200 g.

It is surprising that in embodiments of the invention, the combination of relatively high centrifugal force and long centrifugation times employed to move the aPS cells into and/or through a density barrier do not appear to result in any significant loss in recovery and/or viability (e.g., loss of less than about 10%, 5%, 2%, 1% or less).

Any suitable density barrier medium can be used, for example, PERCOLL™, PERCOLL™ Plus, PURESPERM®, ISOLATE™, SUPRASPERM, OPTIPREP™, FICOLL™, FICOLL-PAQUE™, FICOLL-PAQUE™ Plus, FICOLL-PAQUE™ Premium, NYCODENZ®, HISTO-PAQUE™, an iodixanol solution, a sucrose solution, a cesium solution and/or a glycerol solution. The density barrier medium can be of a single density or a density gradient (for example, if it is desirable to isolate other cell types in addition to aPS cells). Those skilled in the art will appreciate that when the density barrier medium is not isotonic, or if the cell suspension liquid is not isotonic, then the density and size of the aPS cells and contaminating cells will change. Use of non-isotonic solutions requires recalculation of the aPS cell specific gravity and size, and the specific gravity and size of contaminating cells, to determine density barrier specific gravity and to set the centrifugation parameters (height of fluids, centrifugal force, and centrifugation time).

The density barrier medium can have any suitable density to result in the desired level of purity of the isolated aPS cells. In representative embodiments, the density barrier medium has a specific gravity of at least about 1, 1.01, 1.02, 1.03, 1.04, 1.05, 1.06, 1.07, 1.08, 1.09, 1.1, 1.105, 1.11, 1.115, 1.12, 1.125, 1.130, 1.135 or 1.14 although other specific gravities can be used. In illustrative embodiments, the density barrier medium has a specific gravity from about 1, 1.05, 1.06, 1.07, 1.08, 1.09, 1, 1.1 or 1.11 to about 1.12, 1.13, 1.14, 1.15, 1.16, 1.17, 1.18, 1.19 or 1.2 or more (including any combination of lower and upper values). In representative embodiments, the density barrier medium has a specific gravity that is greater than 1.08 g/mL.

Those skilled in the art will appreciate that the specific gravity of the density barrier medium can vary; however, a lower specific gravity may give rise to a higher level of contamination by cells with lower specific gravities than aPS cells. In embodiments of the invention, the density barrier medium has a specific gravity that is at least about 0.01, 0.015 or 0.02 greater than the specific gravity of the densest contaminating cell type. Further, the density of the barrier can be adjusted to isolate subpopulations of aPS cells, e.g., the smaller cells having a diameter in the range of about 0.5 or 1 micron to about 1.5, 2, 2.5 or 3 microns. Without wishing to be held to any theory of the invention, it appears that the larger the aPS cell, the lower the specific gravity. Thus, for example, using a density barrier medium with a specific gravity of about 1, 1.01, 1.02, 1.03, 1.04, 1.05, 1.06, 1.07, 1.08, 1.09, 1.1 or 1.11 may isolate more of the larger aPS cells than a density barrier medium with a specific gravity of about 1.12, 1.13 or 1.14 or higher.

Additional purification steps can be employed prior to and/or after the density purification. For example, the method can further comprise using negative selection to remove contaminating (non-aPS) cells and/or positive selection to enrich for aPS cells. Suitable methods, such as immunopurification, flow cytometry, elutriation and/or other continuous flow separation methods are known to those skilled in the art. For example, following density centrifugation of a blood sample (this term including processed blood samples), contaminating cells can be separated from aPS cells by positive and/or negative selection. In another exemplary embodiment, the method can further comprise using elutriation after removal of platelets by use of a density barrier medium with a density of about 1.06 or 1.07 g/mL.

For example, to reduce the number of contaminating cells, and thus achieve a higher purity of aPS cells, immunopurification methods such as immunomagnetic depletion can be used, based on the principle that contaminating cells that are not aPS cells can be identified by the expression of markers not expressed by aPS cells (or expressed by aPS cells only at low levels). Those skilled in the art will appreciate that the term "marker" includes protein and glycoprotein markers and, optionally nucleic acid (e.g., mRNA) markers. To illustrate, contaminating hematopoietic lineage cells can be depleted with antibodies against CD45, platelets with antibodies against CD61, and/or red blood cells with antibodies against CD235a, or any other antibody selective for any other contaminating cell type. When aPS cell isolation is done from a biological fluid or tissue other than blood, then the appropriate immunogenic markers of contaminating cells from that tissue or fluid can be used. Appropriate technologies for immunopurification include, but are not limited to MACS® cell separation (Miltenyi Biotec), EASYSEP® and ROBOSEP® (Stemcell Technologies), Quadrasep QMC™ quadrupole magnetic sorter (Ikotech), and/or microfluidic immunogenic cell separation.

Another approach involves the use of positive selection, which can employ the technologies described above with respect to negative selection. With positive selection, however, the aPS cells are identified and enriched by markers (e.g., cell surface markers) not expressed by other contaminating cells (or expressed only at low levels), for example, SSEA4 (humans) and SSEA1 (mouse).

In particular embodiments, the isolation method comprises placing a centrifuge tube with an opening formed in the bottom portion thereof within a larger centrifuge tube. The size of the opening formed in the inner tube is not critical and may be, for example, from about 1 mm to about 5 mm (e.g., about 1 mm, 1.5 mm, 2 mm, 2.5 mm, 3 mm, 3.5 mm, 4 mm, 4.5 mm, or 5 mm and any range therein), or larger up to the inside diameter of the inner centrifuge tube. In embodiments, two or more openings can be formed in the bottom portion of the inner centrifuge tube. Thus, the number of openings can be about 1, 2, 3, 4, 5, 6, 7, 8, 9 and/or 10, or more.

The inner tube is optionally attached to the outer tube by any of a number of methods, including without limitation screwing into the outer tube, resting on the top of the outer tube and/or snapping into the outer tube, etc.

Further, in embodiments, the inner tube comprises a filter or frit with pores sufficiently large (e.g., at least about 4, 5 or 6 microns) so that the aPS cells can pass therethrough. The filter or frit can facilitate layering the cell suspension over the density barrier medium by reducing mixture of the sample medium with the density barrier medium. According to this embodiment, the density barrier medium in the inner centrifuge tube can optionally come to a level that covers the filter or frit and does not rise substantially therebeyond (e.g., less than about 1 cm, 0.5 cm, 0.25 cm, 0.2 cm, 0.15 cm, 0.1 cm).

The density barrier medium is added to both tubes and is in communication between tubes, e.g., it is added to a sufficient level such that it is contained in both the inner and outer tubes and is in communication through the opening in the bottom portion of the inner centrifuge tube. In representative embodiments, by the geometry of the tubes and in particular the fitting of the upper regions of the tube, the inner tube is locked in position relative to the outer tube during centrifugation. Optionally, the inner tube may lock into a collar or annular fitting provided by the outer tube and/or the inner tube may be provided with an annular flange or collar that locks into the outer tube. In embodiments, the level of the density barrier medium in the inner tube and the level of the density barrier medium in the outer tube are substantially the same (e.g., less than about a 35%, 30%, 25%, 20%, 15%, 10%, 5% or less difference). In exemplary embodiments, simple visual inspection provides no perception of a difference of the levels.

The method further comprises layering the mixture of animal cells above the density barrier medium in the inner tube, which is optionally enclosed (e.g., capped and/or sealed). Typically, due to the relatively low density of the sample medium and the relatively high density of the density barrier medium, addition of the sample only results in a modest or slight movement of the density barrier medium from the opening formed in the bottom of the inner tube into the outer tube. Generally, however, it does not result in any portion of the sample comprising the mixture of animal cells moving into the outer tube (e.g., prior to centrifugation). In embodiments, the level of the sample medium plus the density barrier medium in the inner tube and the level of the density barrier medium in the outer tube remain substantially the same (generally, however, the level in the inner tube is slightly higher). That is, the sample medium "floats" above the density barrier medium in the inner tube.

The method optionally further comprises the inner tube being enclosed prior to density centrifugation (e.g., by a seal and/or a cap), optionally to create a vacuum, so that both the inner tube and the outer tube do not communicate outside the inner tube and the outer tube. The tube may be enclosed after sample addition and/or the sample may be added to the enclosed tube, for example, via a port and/or injection through the top.

The method further comprises centrifuging the "tube in a tube" comprising the sample for a sufficient time and centrifugal force (e.g., calculated using Stokes' Equation) so that the aPS cells move downward into the density barrier medium and out of the inner tube. In representative embodiments, the sample is centrifuged until the aPS cells enter the density barrier medium in the region beneath the inner tube and within the outer tube. By contrast, the lower density sample medium and lower density cells to not move out of the inner tube. In representative embodiments, the levels of the sample medium and/or the density barrier medium remain the same before, throughout, and after centrifugation. Optionally, the aPS cells traverse the density barrier medium and, as a further option, may be pelleted at the bottom of the outer centrifuge tube. After centrifugation, the inner tube (which contains most of the contaminating cells) is removed, leaving the aPS cell fraction behind in and/or below the density barrier medium in the outer tube.

The "tube in a tube" method can advantageously be practiced to reduce contamination of the isolated aPS cells from other, less dense cells. In representative embodiments, the biological sample is whole blood, and the red blood cells are substantially removed (e.g., at least about 50%, 60%, 70%, 80%, 90%, 95% or more) with the inner tube and, optionally, the method does not comprise any additional steps for lysis and/or substantial removal of red blood cells. In representative embodiments, there are no additional steps (e.g., before and/or after density centrifugation) to remove contaminating (i.e., non-aPS cells). Further, in representative embodiments, aPS cells isolated according to the "tube in a tube" method are at least about 50%, 60%, 70%, 80%, 90%, 95%, 96%, or 97% or more pure following the centrifugation step, optionally without any other techniques being employed to lyse and/or substantially remove red blood cells and/or other contaminating cell types (e.g., before and/or after density centrifugation). Those skilled in the art will appreciate that the isolation method may employ wash steps to remove density barrier material and other ancillary procedures that may incidentally remove some contaminating cells.

Accordingly, in representative embodiments, the invention provides a method for isolating aPS cells from a mixture of animal cells, wherein the mixture of animal cells is centrifuged over a density barrier medium within an inner centrifuge tube, wherein the inner centrifuge tube comprises an opening formed in the bottom thereof and is positioned in an outer centrifuge tube, such that the density barrier medium is in communication between the inner and outer centrifuge tubes, and wherein there is a space between the bottom of the inner centrifuge tube and the bottom of the outer centrifuge tube, and wherein the inner centrifuge tube is capped. The mixture of animal cells is centrifuged such that the aPS cells migrate or travel (e.g., migrate or travel downward) through the density barrier medium in the inner centrifuge tube, then out of the inner centrifuge tube through the opening formed in the bottom thereof and into the density barrier medium to a position within and/or below the density barrier medium in the outer centrifuge tube (e.g., in the space between the bottom of the inner centrifuge tube and the bottom of the outer centrifuge tube).

Following centrifugation, the method generally comprises collecting the fraction within and/or below the density barrier medium containing the aPS cells. In embodiments of the invention, the aPS cells travel into the density barrier medium in the outer centrifuge tube, and optionally through the density barrier medium to a position below the density barrier medium (optionally to form a pellet in the bottom of the outer centrifuge tube).

According to the embodiments of the "tube in a tube" method, the density centrifugation is carried out without the aPS cells forming a pellet, which will generally shorten centrifugation times as compared with a method in which the aPS cells travel out through the opening in the bottom of the inner centrifuge tube, through the density barrier medium and form a pellet at the bottom of the outer centrifuge tube.

In representative embodiments, the method of collecting the fraction containing the aPS cells comprises removing the inner centrifuge tube from the outer centrifuge tube, wherein the outer centrifuge tube comprises the fraction containing the aPS cells.

In embodiments, the mixture of animal cells has not been treated to lyse and/or remove red blood cells prior to density centrifugation.

In embodiments, the red blood cells in the mixture of animal cells are substantially retained (e.g., at least about 50%, 60%, 70%, 80%, 90%, 95%, 96%, 97%, 98%, 99% or more) within the inner centrifuge tube.

In embodiments, less than about 50%, 40%, 30%, 20%, 10%, 5%, 4%, 3%, 2%, 1% or fewer of the red blood cells in the mixture of animal cells are recovered in the fraction containing the aPS cells.

In embodiments, the contaminating (non-APS) cells in the mixture of animal cells are substantially retained (e.g., at least about 50%, 60%, 70%, 80%, 90%, 95% or more) within the inner centrifuge tube.

In embodiments, less than about 50%, 40%, 30%, 20%, 10%, 5%, 4%, 3%, 2%, 1% or fewer of the contaminating cells (non-aPS cells) in the mixture of animal cells are recovered in the fraction containing the aPS cells.

One illustrative method using density centrifugation to isolate aPS cells from blood (e.g., peripheral and/or cord blood) comprises obtaining a blood sample from an animal subject, centrifuging the sample for a time based on Stokes' Equation at a centrifugation force of 1000 g (~10000 Newtons) for a sufficient time interval for all aPS cells of diameter ≥1 micron to migrate into the density barrier (e.g., PERCOLL™) and/or to a position below the density barrier, with a density of about 1.12 g/mL (specific gravity=~1.12; this density being greater than most peripheral blood cells in an isotonic solution). Centrifugation can be followed by collecting the fraction containing the aPS cells within and/or under the density barrier (e.g., a pellet); and optionally using immunomagnetic and/or flow cytometry methods to remove any remaining contaminating cells.

As an alternative embodiment to isolate aPS cells from biological samples, immunopurification methods may be used directly on whole blood, after lysis of red blood cells and/or or after density separation. In particular embodiments, immunopurification based on immunomagnetic separation, for example, using the Quadrasep QMC™ quadrupole magnetic sorter (Ikotech) is employed. According to this embodiment, cells are labeled with appropriate antibodies that target white blood cells, platelets, and/or red blood cells and that do not target aPS cells (or do so only to a minor extent), using methods known to those skilled in the art. In this embodiment unwanted cells are labeled with an appropriate antibody that is attached to a small magnetic bead, and then the cell suspension is processed by a magnetic sorter. This method can also be utilized to isolate aPS cells from biological fluids and tissues other than blood.

In an alternative method, positive selection is used by labeling the aPS cells with antibodies against SSEA4 or TRA-1-60 (e.g., expressed on the cell surface) or antibodies against any other antigen (e.g., cell-surface antigen) associated with pluripotent stem cells that are expressed by aPS cells and are not expressed by other cells (or only at low levels). Suitable markers can be selected depending on tissue type or body fluid and/or the likely contaminating cells. In one embodiment, the antibodies are attached to magnetic beads and then are subject to immunomagnetic separation, for example, using the Quadrasep QMC™ quadrupole magnetic sorter (Ikotech). Another approach uses positive selection based on immunomagnetic labeling of cells and immunomagnetic separation[28] or based on a microfluidics platform and antibody labeled microposts such as the CTC-Chip (modified to detect aPS-expressed antigens)[29].

Elutriation can also be used prior to and/or after density purification. For example, if a density barrier medium of greater than about 1.08 g/mL (e.g., about 1.09, 1 or 1.1 g/mL) is used for density centrifugation, the fraction within and/or under the density barrier medium (e.g., a pellet) that contains the aPS cells may have a high proportion of contaminating cells. However, contamination by platelets should be relatively low. Elutriation can be used as a subsequent isolation procedure to further purify the aPS cells.

In representative embodiments, following the density purification step, the fraction (e.g., pellet) containing the aPS cells is substantially free of red blood cells (e.g., the red blood cells generally do not travel into and/or below the density barrier medium). According to this embodiment, less than about 25%, 20%, 15%, 10%, 9%, 8%, 7%, 6%, 5%, 4%, 3%, 2% or 1% or even less of the red blood cells in the cell sample subject to density centrifugation are recovered in the fraction containing the aPS cells. In embodiments, only a negligible or insignificant number of red blood cells, or even no detectable red blood cells, are recovered in the fraction containing the aPS cells. In alternative embodiments, the red blood cells are substantially lysed and/or removed prior to density centrifugation, for example, at least about 50%, 60%, 70%, 80%, 90%, 95%, 96% or 97% or more lysed and/or removed (i.e., the mixture of animal cells subject to density centrifugation is substantially free of red blood cells).

In representative embodiments, the methods of the invention result in at least about 50%, 60%, 70%, 75%, 80%, 85%, 90%, 95%, 96% or 97%, or any other value therebetween or a lower or greater value of the isolated cells being aPS cells.

In embodiments of the invention, at least about 50%, 60%, 70%, 75%, 80%, 85%, 90%, 95%, 96% or 97% or any other value therebetween or a lower or greater value of the aPS cells in the cell mixture are recovered by the isolation method.

According to the present invention, the isolated aPS cells generally express one or more pluripotency genes (e.g., associated with stemness), for example, OCT4 and, optionally, one or more other genes that characterize pluripotent stem cells (including homologs from other species). In embodiments of the invention, OCT4 is expressed in the nucleus. In embodiments of the invention, the aPS cells express one or more of OCT4 (e.g., in the nucleus), COMMD3, DNMT3B, EBAF, FGF4, GABRB3, GBX2, GRB7, IGFBP2, IFITM1, IMP2, KIT, LEFTB, LEFTY1, LEFTY2, LIN28, NODAL, NOGGIN, NR6A1, SEMA3A, SOX2, SSEA4, SSEA1, TERT, UTF1, TRA-1-60, TRA-1-80, and ZFP42 (these terms include homologs from other species).

In representative embodiments, the isolation methods of the present invention generally result in a population of aPS cells having a smaller median and/or mean diameter than stem cells isolated by previously reported methods. For example, in nonlimiting embodiments of the invention, the aPS stem cells have a median and/or mean diameter in the range of about 0.5 or 1 micron to about 2, 2.5 or 3 microns.

In representative embodiments, the isolation methods of the present invention generally result in a population of aPS cells characterized by their density (as described in more detail herein). For example, in nonlimiting embodiments of the invention, the aPS stem cells have density greater than about 1.1 g/mL.

In representative embodiments, the methods of the invention can be practiced to produce higher yields of aPS cells than prior methods for isolation of other stem cell populations. For example, the invention can be practiced to produce at least about 3000, 4000, 5000, 6000, 7000, 8000, 9000, 10000 or more aPS cells/mL of whole blood.

In representative embodiments, the mixture of animal cells comprises a biological sample from an animal subject, as described further herein. According to this embodiment, optionally the method further comprises obtaining the biological sample from the animal subject.

aPS cells can be isolated from any suitable mixture of animal cells, including biological fluid samples and/or tissue samples from an animal subject and/or samples comprising cultured animal cells. With respect to cultured cells, the methods of the invention can be practiced, for example, to isolate aPS cells, to enrich the aPS cell population (e.g., by removing contaminants) and/or to passage aPS cell cultures.

The term "biological sample" includes biological fluids and tissues taken from a subject. The term "biological sample" further includes biological fluids and tissues that have been processed (e.g., to lyse and/or remove red blood cells or other contaminating cells and/or to release cells from tissues). Exemplary biological fluids that can be used for the isolation of aPS cells include without limitation blood (e.g., peripheral blood and/or cord blood), plasma, serum, bone marrow, lymph, tears, urine, breast milk, seminal fluid, saliva, amniotic fluid, bronchial lavage, cerebrospinal fluid, pleural fluid, peritoneal fluid and/or colostrum. Suitable biological tissues include, without limitation, neural tissue (e.g., brain, eyes), liver, kidney, fat, skeletal muscle, heart, placenta, spleen, stomach, small intestine, colon, rectum, lung, pancreas, epithelium (e.g., olfactory epithelium), reproductive tissue (e.g., testis, ovary, uterus, vagina, cervix and/or fallopian tube), bone marrow, dental pulp, gum, hair follicle, nail bed, blood vessel, connective tissue, skin, umbilical cord and/or an embryo. Tissues can be from postnatal (e.g., adult), neonatal and/or embryonic subjects. Those skilled in the art are familiar with methods of releasing cells from tissue samples (e.g., by enzymatic digestion to remove extracellular matrix).

When the biological sample is blood, the blood sample can optionally be treated to reduce the number of red blood cells (e.g., prior to density centrifugation if density centrifugation is employed in the isolation method) by any suitable means known in the art. For example, a chemical agent can be added to lyse the red blood cells. In an exemplary embodiment, most red blood cells are removed by red blood cell lysis employing a hypotonic solution such as an ammonium chloride solution, or other standard red blood cell lysis methods well known to those experienced in the art. Optionally, the hypotonic solution and blood sample can both be at about 37° C. for the entire procedure to increase efficacy of red blood cell lysis. In addition, in the case of blood samples, the sample can be treated after collection to prevent coagulation.

Peripheral blood samples may be obtained through routine venipuncture and collected into a tube containing an anticoagulant, such as, but not limited to, heparin, EDTA, or sodium citrate. Optionally, the blood can be kept at room temperature (e.g., about 10-35° C.) or under cold conditions (e.g., about 37° C. or from about 1-10° C.) until processing. In a further representative embodiment, the blood is processed within about 3 hours of collection (although longer storage will still yield viable cells).

Other organs, tissues, or body fluids may be obtained by routine methods known to those skilled in the art, and processed as needed so as to release cells into suspension.

Specific to peripheral blood, it is reasonable to assume that a proportion of aPS cells, like other peripheral white blood cells, are subject to margination, i.e., they are adherent to the endothelial cells of blood vessels. Moderate exercise leads to transient increases in circulating white blood cells through a process of demargination, mediated by shear forces, discharge of lymph, effects of epinephrine, and other factors. As known in the art, numerous drugs, including various steroids, epinephrine, etc. will also induce demargination. Accordingly, in representative embodiments, to enhance the yield of aPS cells, the subject from which the biological sample is collected engages in moderate exercise (e.g., climbing stairs, treadmill, brisk walking, or slow jogging) for at least one to twenty minutes and/or is administered a drug that induces demargination (e.g., prednisone or other steroids and/or epinephrine) prior to collecting the peripheral blood sample.

Further, aPS cells reside in the bone marrow and the use of methods known to mobilize other types of stem cells from bone marrow to increase the number of circulating aPS cells can be used[27] (e.g., administration of G-CSF).

aPS Cells

The invention also provides an isolated aPS cell and populations and cultures thereof. In embodiments of the invention, the aPS cell is isolated according to a method of the invention as described herein.

The inventors are the first to identify a population of stem cells, designated as "aPS cells" that have a specific gravity greater than other cells in blood as well as most other animal cells. aPS cells are small, with most having a diameter of about 0.5 or 1 micron to about 2, 2.5, 3 or 4 microns. Additionally, in long-term culture most aPS cells have a diameter in the range of about 0.5 or 1 micron to about 2, 2.5, 3 or 4 microns.

Accordingly, the invention provides an isolated population of aPS cells from an animal subject, wherein the aPS cells have a mean and/or median diameter of about 0.5 or 1 micron to about 2, 2.5, 3 or 4 microns with a range of about 0.5 or 1 micron to about 5 or 6 microns. Optionally, the aPS cells in the isolated population have a density greater than about 1.08 g/mL.

The invention further provides a culture of aPS cells, wherein the aPS cells have a mean and/or median diameter in the range of about 0.5 or 1 micron to about 2, 2.5, 3 or 4 microns with a range of about 0.5 or 1 micron to about 5 or 6 microns. Optionally, the aPS cells in the culture have a density greater than about 1.08 g/mL.

The population or culture of aPS cells generally expresses one or more pluripotency genes associated with stemness (e.g., expression of OCT4 in the nucleus and/or SSEA4 on the cell surface or the homologous genes in non-human animals). In embodiments of the invention, the aPS cells in the population or culture have one or more characteristics selected from: tightly packed heterochromatin, a nucleus that stains with DNA specific (e.g., DRAQ5™) and/or non-specific (e.g., DAPI) nucleic acid stains, exclusion of trypan blue (i.e., trypan blue negative) and/or use of glucose as a carbon source. In further representative embodiments, the aPS cell is adherent in culture. Those skilled in the art will appreciate that characteristics, phenotypes, gene expression patterns and the like of a population or culture of cells refers to the population or culture as a whole, although individual cells may not exhibit the particular characteristic, phenotype and/or gene expression pattern. In representative embodiments, at least about 50%, 60%, 70%, 80%, 90%, 95%, 96%, 97% or more of the aPS cells in the population or culture exhibit one or more of the characteristics, phenotypes and/or gene expression patterns described herein.

In representative embodiments, the population or culture of aPS cells is at least about 50%, 60%, 70%, 80%, 90%, 95%, 96%, 97% or more pure (e.g., at least about 50%, 60%, 70%, 80%, 90%, 95%, 96%, 97% of the cells are aPS cells).

In embodiments of the invention, the population or culture of aPS cells has been cultured (e.g., continuously cultured) for a period of time (e.g., at least about 1 week, 2 weeks, 3 weeks, one month, two months; three months, four months, six months, eight months, ten months, one year) and expresses one or more pluripotency genes associated with stemness, e.g., one or more of OCT4 (e.g., in the nucleus), COMMD3, DNMT3B, EBAF, FGF4, GABRB3, GBX2, GRB7, IGFBP2, IFITM1, IMP2, KIT, LEFTB, LEFTY1, LEFTY2, LIN28, NODAL, NOGGIN, NR6A1, SEMA3A, SOX2, SSEA4, SSEA1, TERT, UTF1, TRA-1-60, TRA-1-80, and ZFP42. In embodiments, the population or culture of aPS cells expresses OCT4 (e.g., in the nucleus) and one or more pluripotency genes associated with stemness, e.g., one or more of COMMD3, DNMT3B, EBAF, FGF4, GABRB3, GBX2, GRB7, IGFBP2, IFITM1, IMP2, KIT, LEFTB, LEFTY1, LEFTY2, LIN28, NODAL, NOGGIN, NR6A1, SEMA3A, SOX2, SSEA4, SSEA1, TERT, UTF1, TRA-1-60, TRA-1-80, and ZFP42.

In embodiments of the invention, less than about 20%, 15%, 10%, 5%, 3%, 2%, 1% or even less of the cells are differentiated and/or have lost pluripotency as determined by morphology and/or expression of markers of pluripotency (e.g., as described herein), markers of commitment to particular lineages, and/or markers associated with differentiation (e.g., PAX6 as a marker of neural differentiation).

Cell Culture

A suitable cell culture medium and system for aPS cells supports the survival and expansion of aPS cells. In representative embodiments, the cell culture medium provides for the survival and expansion of aPS cells without significant levels of differentiation (e.g., embryoid body formation), assuming that the medium is replenished and/or the cells passaged at suitable intervals. In embodiments of the invention, less than about 20%, 15%, 10%, 5%, 3%, 2%, 1% or even less of the cells in culture are differentiated and/or have lost pluripotency as determined by morphology and/or expression of markers of pluripotency, markers of commitment to particular lineages, and/or markers associated differentiation.

In embodiments of the invention, the culture of aPS cells has been cultured (e.g., continuously cultured) for a period of time (e.g., at least about 1 week, 2 weeks, 3 weeks, one month, two months, three months, four months, six months, eight months, ten months or one year) and/or substantially all of the cells (e.g., at least about 80%, 85%, 90%, 95%, 97%, 98%, 99% or more) express one or more pluripotency genes associated with stemness [e.g., one or more of OCT4 (e.g., in the nucleus), COMMD3, DNMT3B, EBAF, FGF4, GABRB3, GBX2, GRB7, IGFBP2, IMP2, IFITM1, KIT, LEFTB, LEFTY1, LEFTY2, LIN28, NODAL, NOGGIN, NR6A1, SEMA3A, SOX2, SSEA4, SSEA1, TERT, UTF1, TRA-1-60, TRA-1-80, and ZFP42] and/or are not aggregated into embryoid bodies. In embodiments, substantially all of the cells express OCT4 (e.g., in the nucleus) and one or more pluripotency genes associated with stemness (e.g., one or more of COMMD3, DNMT3B, EBAF, FGF4, GABRB3, GBX2, GRB7, IGFBP2, IMP2, IFITM1, KIT, LEFTB, LEFTY1, LEFTY2, LIN28, NODAL, NOGGIN, NR6A1, SEMA3A, SOX2, SSEA4, SSEA1, TERT, UTF1, TRA-1-60, TRA-1-80, and ZFP42) and/or are not aggregated into embryoid bodies.

In representative embodiments, the culture medium comprises: (a) one or more mitogenic factors; (b) one or more cell survival factors; (c) selenium (optionally in the form of selenite); (d) one or more simple sugars (e.g., a 6-carbon sugar such as glucose and/or fructose) and/or (e) phosphate. For example, glucose can be present in the medium at a concentration of at least about 3500, 4000, 5000, 6000 or 6500 mg/L. In embodiments of the invention, the concentration of glucose is from about 3500, 4000, 5000, 6000, 7000, 8000, 9000 or 10,000 mg/L to about 10,000, 12,000, 15,000, 20,000, 30,000, 50,000, 70,000, 80,000 or 100,000 mg/L or more. In embodiments of the invention, the glucose concentration is about 10,000 mg/L.

In other illustrative embodiments, the culture medium comprises: (a) one or more mitogenic factors; (b) one or more cell survival factors; (c) selenium (optionally in the form of selenite); (d) optionally, one or more simple sugars (e.g., a 6-carbon sugar such as glucose and/or fructose) and (e) optionally, ascorbic acid.

Any suitable mitogenic factor can be included in the culture medium, including but not limited to epidermal growth factor (EGF; e.g., about 0.1-500 ng/mL), transformed growth factor-α (TGF-α; e.g., about 0.5-50 ng/mL), transformed growth factor-β (TGF-β; e.g., about 0.1-50 μg/mL), Nodal (e.g., about 0.01-2 ng/mL), Noggin (e.g., about 0.1-500 ng/mL), leukocyte inhibitory factor (LIF; e.g., about 10-10,000 U/mL), Activin A (e.g., about 0.1-500 ng/mL), stem cell factor (SCF; e.g., about 0.5-50 ng/mL), heregulin (NRG1) (e.g. about 0.1-500 ng/mL), hepatocyte growth factor (HGF). (e.g. about 0.1-500 ng/mL), platelet-derived growth factor (e.g., PDGF; about 0.05-1000 ng/mL) and/or fibroblast growth factor-2 (FGF2; e.g., about 0.1-500 ng/mL).

In representative embodiments, the culture medium does not comprise TGF-β and/or retinoic acid.

In embodiments of the invention, the cell survival factor comprises transferrin (e.g., about 0.01-2 mg/mL), insulin (e.g., about 0.001-1 mg/mL), selenium (e.g. about 0.01-2 mg/mL; optionally in the form of selenite), platelet-derived growth factor (e.g., PDGF; about 0.05-1000 ng/mL), insulin-like growth factor 1 (e.g., about IGF-1; 0.5-500 ng/mL) and/or insulin-like growth factor 2 (e.g., about IGF-2; 0.1-100 ng/mL). The PDGF can be PDGF-AA, -AB and/or -BB.

In one exemplary embodiment, the culture medium comprises a basal medium (e.g., Euromed-N; Euroclone) supplemented with EGF (e.g., about 2-20 ng/mL), FGF2 (e.g., about 2-20 ng/mL), and optionally including 0.6% glucose, putrescine (e.g., about 10 mM), progesterone (e.g., about 0.002 mM), selenium (e.g., about 0.01-2 mg/mL, for example, about 0.003 mM, optionally in the form of selenite), insulin (e.g., about 0.001-1 mg/mL, for example, about 0.09 mM), transferrin (e.g., about 0.01-2 mg/mL, for example, about 1 mM), and/or ascorbic acid (e.g., about 0.1-1000 μg/mL, for example, about 80 μg/mL) (Sigma). Alternatively N2, N2 plus and/or B27 may be substituted for the insulin, transferrin, selenium, putrescine, and progesterone. Hydrocortisone (e.g., about 100 nM) may be substituted for the progesterone. TGFβ (e.g., about 2 μg/L) or Nodal (e.g., about 100 μg/L) may be substituted for EGF. DMEM/F12, advanced MEM, opti-MEM or MEM alpha may be substituted for Euromed-N in this medium Optionally, thrombin (e.g., about 1 unit/L) may be included. In embodiments, albumin (e.g., BSA) and/or β-mercaptoethanol are not included in the medium. In embodiments of the invention, serum and/or plasma are not included in the medium.

In representative embodiments, the culture medium has a calcium concentration of about 1.05 mM, a glucose concentration of at least 6500 mg/L, and a HEPES concentration of about 1325 mg/L or less, although other concentrations may be used if cell growth is not compromised.

In further representative embodiments, the culture medium comprises a basal medium (e.g., DMEM/F12) supplemented with insulin (e.g., about 0.001-1 mg/mL, for example, about 0.09 mM), transferrin (e.g., about 0.01-2 mg/mL, for example, about 1 mM) and selenium (e.g., about 0.01-2 mg/mL, for example, about 0.003 mM, optionally in the form of selenite) as well as FGF2 (e.g., about 0.1-500 ng/mL, for example, about 100 ng/mL) and/or PDGF (e.g., PDGF-AA, -AB and/or -BB; about 0.05-1000 ng/mL, for example about 10 ng/mL). Alternatively N2, N2 plus and/or B27 may be substituted for the insulin, transferrin and selenium. Optionally, the culture medium comprises ascorbic acid (e.g., about 0.1-1000 µg/mL, for example, about 64 µg/mL). Optionally, the culture medium comprises a simple sugar (e.g., a 6-carbon sugar such as glucose and/or fructose). In representative embodiments, the basal medium is DMEM/F12, Euromed-N, advanced MEM, opti-MEM or MEM alpha. Optionally, thrombin (e.g., about 1 unit/L) may be included. In embodiments, albumin (e.g., BSA) and/or β-mercaptoethanol are not included in the medium. In embodiments of the invention, serum and/or plasma are not included in the medium.

In embodiments of the invention, the medium further comprises a steroid, for example a corticosteroid (e.g., hydrocortisone), dexamethasone, and/or progesterone.

In representative embodiments, the medium further comprises one or more of putrescine (e.g., about 0.1-200 µg/mL), progesterone (e.g., about 0.1-200 ng/mL), hydrocortisone (e.g., about 0.1-2000 nM), ascorbic acid (e.g., about 0.1-1000 µg/mL), thrombin (e.g., about 0.1-50 units/L), lipids, nucleotides and nucleic acids.

In embodiments of the invention, the medium further comprises HEPES, hypoxanthine, linoleic acid, lipoic acid, phenol red, sodium pyruvate and thymidine.

In embodiments of the invention, the phosphate concentration in the medium is at least about 0.5, 0.75 or 1 mM. In embodiments of the invention, the phosphate concentration in the medium is from about 0.5, 0.75 or 1 mM to 2, 3, 4, 5 10, 20, 50, 100, 200, 500 or 1000 mM.

In embodiments, the culture medium comprises one or more simple sugars, for example, one or more 6-carbon and/or 5-carbon sugars. Exemplary sugars include without limitation glucose, fructose, galactose and/or mannose (all 6-carbon) and/or ribose (5-carbon).

In embodiments of the invention, the culture medium comprises one or more amino acids (e.g., glycine, L-alanine, L-arginine, L-asparagine, L-aspartic acid, L-cysteine, L-glutamic acid, L-histidine, L-isoleucine, L-leucine, L-lysine, L-methionine, L-phenylalanine, L-proline, L-serine, L-threonine, L-tryptophan, L-tyrosine and/or L-valine).

In embodiments of the invention, the medium further comprises an inorganic salt (e.g., a salt of calcium, copper, iron, magnesium, potassium, sodium and/or zinc).

In embodiments of the invention, the medium comprises a vitamin (e.g., choline, vitamin B7, vitamin B5, folate, folic acid, inositol, nicotinamide, vitamin B6, riboflavin, thiamine, and/or vitamin B12).

In embodiments, the culture medium comprises a suitable buffer, e.g., HEPES, optionally at a concentration of about 1325 mg/L or less. Generally, the pH of the medium is maintained in the physiological range (e.g., about pH 7.4).

In embodiments of the invention, the culture medium comprises Euromed-N (Euroclone) or DMEM/F12 (i.e., as the basal medium). A comparison of the composition of Euromed-N with DMEM/F12 is shown below.

|  | EuroMed-N | DMEM/F12 |
|---|---|---|
| Amino acids: | | |
| Glycine | 18.75 mg/l | 18.75 mg/l |
| L-Alanine | 4.45 mg/l | 4.45 mg/l |
| L-Arginine + HCl | 147.5 mg/l | 147.5 mg/l |
| L-Asparagine + H2O | 7.5 mg/l | 7.5 mg/l |
| L-Aspartic acid | 6.65 mg/l | 6.65 mg/l |
| L-Cysteine + HCl + H2O | 17.56 mg/l | 17.56 mg/l |
| L-Cystine | 24 mg/l | 24 mg/l |
| L-Glutamic acid | 7.35 mg/l | 7.35 mg/l |
| L-Histidine + HCl + H2O | 31.48 mg/l | 31.48 mg/l |
| L-Isoleucine | 54.45 mg/l | 54.45 mg/l |
| L-Leucine | 59.05 mg/l | 59.05 mg/l |
| L-Lysine + HCl | 91.25 mg/l | 91.25 mg/l |
| L-Methionine | 17.25 mg/l | 17.25 mg/l |
| L-Phenylalanine | 35.48 mg/l | 35.48 mg/l |
| L-Proline | 17.25 mg/l | 17.25 mg/l |
| L-Serine | 26.25 mg/l | 26.25 mg/l |
| L-Threonine | 53.45 mg/l | 53.45 mg/l |
| L-Tryptophan | 9.02 mg/l | 9.02 mg/l |
| L-Tyrosine | 38.7 mg/l | 38.7 mg/l |
| L-Valine | 52.85 mg/l | 52.85 mg/l |
| Inorganic salt | | |
| Calcium chloride dehydrate | 1.05 mM | 1.05 mM |
| Cupric sulphate pentahydrate | 0.00125 mg/l | 0.0013 mg/l |
| Ferric nitrate nonhydrate | 0.05 mg/l | 0.05 mg/l |
| Ferrous sulphate hextahydrate | 0.417 mg/l | 0.417 mg/l |
| Magnesium chloride hexahydrate | 61 mg/l | 61 mg/l |
| Magnesium sulfate heptahydrate | 100 mg/l | 48.84 mg/l |
| Potassium chloride | 311.8 mg/l | 311.8 mg/l |
| Sodium bicarbonate | 1250 mg/l | 1250 mg/l |
| Sodium chloride | 6999.5 mg/l | 6999.5 mg/l |
| Sodium dihydrogenate phosphate monohydrate | 62.5 mg/l | 0 mg/l |
| Sodium phosphate dibasic anhydrous | 71 mg/l | 62.5 mg/l |
| Zinc sulphate heptandrate | 0.43 mg/l | 0.432 mg/l |
| Vitamins: | | |
| Choline chloride | 8.98 mg/l | 8.98 mg/l |
| D-Biotin | 0.00365 mg/l | 0.0035 mg/l |
| D-Ca pantothenate | 2.24 mg/l | 2.24 mg/l |
| Folic acid | 2.65 mg/l | 2.65 mg/l |
| L-Inositol | 12.6 mg/l | 12.6 mg/l |
| Nicotinamide | 2.0185 mg/l | 2.02 mg/l |
| Pyridoxal + HCl | 2 mg/l | 2 mg/l |
| Pyridoxine + HCl | 0.031 mg/l | 0.031 mg/l |
| Riboflavin | 0.219 mg/l | 0.219 mg/l |
| Thiamine + HCl | 2.17 mg/l | 2.17 mg/l |
| Vitamin B12 | 0.68 mg/l | 0.68 mg/l |
| Other: | | |
| D-Glucose | 6660 mg/l | 3151 mg/l |
| HEPES | 1325 mg/l | mg/l |
| Hypoxanthine | 2.05 mg/l | 2.1 mg/l |
| Linoleic acid | 0.042 mg/l | 0.042 mg/l |
| Lipoic acid | 0.105 mg/l | 0.15 mg/l |
| Phenol red | 8.1 mg/l | 8.1 mg/l |
| Sodium pyruvate | 55 mg/l | 55 mg/l |
| Thymidine | 0.365 mg/l | 0.365 mg/l |

Other suitable basal media include, without limitation, advanced MEM, opti-MEM or MEM alpha medium.

In general, the basal medium provides the minimal components for cell survival and expansion and often includes, for example, electrolytes, lipids, a nitrogen source (e.g., amino acids), insulin, transferrin, vitamins, selenium, a suitable buffer and, optionally, a carbon/energy source (e.g., a 6-carbon sugar such as glucose and/or fructose), other trace elements (e.g., co-factors), nucleotides (or precursors thereof).

The medium may optionally include other nutrients, buffers, hormones, salts, antibiotics, proteins, growth factors and/or enzymes.

In embodiments of the invention, the culture medium does not comprise serum and/or plasma (e.g., is a serum-free medium).

In embodiments of the invention, the culture medium does not comprise albumin (e.g., bovine serum albumin [BSA]).

In embodiments of the invention, the culture medium does not comprise β-mercaptoethanol.

As a further option, the cells can be cultured and expanded in any other suitable medium known in the art for the culture and expansion of stem cells, e.g., E8 medium (for example, TeSR™1, mTeSR™1, TeSR™2, or mTeSR™2 media, all available from STEMCELL™ Technologies).

The invention also provides a method of culturing aPS cells, the method comprising culturing a population of aPS cells in a culture vessel containing a medium for expanding the aPS cells and, optionally, maintaining the cells in an undifferentiated state. In embodiments, the aPS cells are isolated according to the methods of the invention. Optionally, the culture medium is a culture medium of the invention. Standard or specialized cell culture incubators are suitable for use in the methods of the invention.

Any suitable vessel can be used for culturing the cells, for example a culture dish, multi-well plate or flask. In some embodiments, the culture vessel is coated with feeder cells and/or a cell substrate. Suitable cell substrates comprise an extracellular matrix protein, optionally, laminin, collagen (e.g., collagen IV), vitronectin, fibronectin, entactin, blebbistatin and/or a synthetic polymer coating such as poly [2-methacryloyloxy)ethyl dimethyl-(3-sulfopropyl) ammonium hydroxide] (PMEDSAH). Suitable cell substrates are commercially available, such as isvitronectin (R&D Systems), MATRIGEL™ and Laminin-511.

Alternatively the cells may be cultured with no substrate (i.e., uncoated) or in suspension culture (e.g., in shaker flasks).

In representative embodiments, the cells are cultured in an atmosphere with a $CO_2$ level of about 5%, with the rest being room air.

In other embodiments, the cells are cultured in an atmosphere with a $CO_2$ level of about 5% and an $O_2$ level of about 5%, with the remainder being mostly nitrogen.

Optionally, the cells are cultured under conditions of high humidity (e.g., at least about 90%, 95%, 87%, 98%, 99% or even 100% saturated).

Typically, the cells are cultured at a physiological temperature (e.g., about 37° C.).

In embodiments of the invention, the culture medium is changed relatively infrequently, for example, prior to the cells become established and expanding rapidly. To illustrate, in representative embodiments, the culture medium is not changed for at least about 2, 3, 4, 5, 6, 8 or more weeks. Those skilled in the art will appreciate that the culture medium may optionally be changed soon after initial plating of the cells (e.g., at around day 1 and day 7 after plating), e.g., to remove dead cells and/or debris. According to embodiments of the invention, the number of aPS cells in culture remains relatively quiescent for about 1, 2, 3, 4, 5, or 6 weeks, then will double within about 60, 70, 80 or 90 to 100, 120, 150, 200 or 250 hours with at least about 70%, 80%, 90%, 95%, 96%, 97%, 98% or higher purity. In embodiments of the invention, the number of aPS cells in culture doubles within about 7 days with at least about 70%, 80%, 90%, 95%, 96%, 97%, 98% or higher purity. Optionally, the aPS cells are isolated according to the methods of the invention.

According to embodiments of the present invention, less than about 20%, 15%, 10%, 5%, 3%, 2%, 1% or even fewer of the cultured cells are differentiated and/or have lost pluripotency as determined by morphology and/or expression of markers of pluripotency, markers of commitment to particular lineages, and/or markers associated with differentiation as are known to those skilled in the art, after culturing (e.g., continuous culture) for a period of at least about 1 week, 2 weeks, 3 weeks, one month, two months, three months, four months, six months, eight months, ten months, or one year and/or substantially all of the cells (e.g., at least about 80%, 85%, 90%, 95%, 97%, 98%, 99% or more) express one or more pluripotency genes associated with stemness, e.g., one or more of OCT4 (e.g., in the nucleus), COMMD3, DNMT3B, EBAF, FGF4, GABRB3, GBX2, GRB7, IGFBP2, IFITM1, IMP2, KIT, LEFTB, LEFTY1, LEFTY2, LIN28, NODAL, NOGGIN, NR6A1, SEMA3A, SOX2, SSEA4, SSEA1, TERT, UTF1, TRA-1-60, TRA-1-80, and ZFP42 and/or are not aggregated into embryoid bodies. Optionally, according to this embodiment, the aPS cells are isolated according to the methods of the invention.

In embodiments of the invention, the aPS cells are at least about 70%, 80%, 90%, 95%, 97%, 98% or more pure after 1 week, 2 weeks, 3 weeks, one month, two months, three months, four months, six months, eight months, ten months, or one year in culture (e.g., continuous culture). Optionally, according to this embodiment, the aPS cells are isolated according to the methods of the invention.

In embodiments of the invention, the aPS cells have a mean and/or median diameter in the range of about 0.5 or 1 to 2, 2.5 or 3 microns after 1 week, 2 weeks, 3 weeks, one month, two months, three months, four months, six months, eight months, ten months, or one year in culture (e.g., continuous culture). Optionally, according to this embodiment, the aPS cells are isolated according to the methods of the invention.

In embodiments of the invention, the method further comprises inducing differentiation of the aPS cell culture. Suitable methods and media for inducing differentiation of aPS cells are known to those skilled in the art of stem cell differentiation, e.g., removing mitogenic factors and/or adding serum to the medium.

Use of aPS Cells

The invention also encompasses methods of using an isolated aPS cell to evaluate (e.g., determine) safety of a compound and/or effectiveness of a compound for treatment of disease (e.g., schizophrenia including schizophrenia associated with 22q11 Deletion Syndrome, bipolar disorder, autism, diabetes or other disorders). In representative embodiments, safety and/or effectiveness is evaluated on the basis of a particular subpopulation of subjects or on an individualized basis.

The invention further contemplates use of an isolated aPS cell to evaluate safety or efficacy of a putative pharmaceutical agent or a putative treatment, or to evaluate manufacturing efficiency, production economics, or successful translation to clinical applications including diagnoses or treatments.

The invention further provides for the use of an isolated aPS cell to evaluate the mechanism underlying a disease or disorder (e.g., schizophrenia including schizophrenia associated with 22q11 Deletion Syndrome, bipolar disorder, autism, diabetes or other disorders) to yield an individualized diagnosis in an animal subject from which the aPS cells were isolated. In embodiments of the invention, mitochondrial activity (e.g., cellular oxygen consumption, mitochondrial network dynamics and/or the abundance of proteins and/or mRNAs associated with mitochondrial function) of the aPS cells are evaluated, optionally the response of one or more of these factors to treatment of aPS cells by drugs or other therapies. For example, it has been reported that mitochondrial function might serve as an endophenotype for schizophrenia (Rosenfeld et al., Perturbation in mitochondrial network dynamics and in complex I dependent cellular respiration in schizophrenia. *Biol. Psychiatry* 69: 980-988, 2011). Mitochondrial respiration, mitochondrial dynamics and mitochondrial protein levels can be determined by any suitable method known in the art, e.g., by oxygraph, confocal microscopy, and immunoblotting, respectively.

The invention also provides methods of using an isolated aPS cell to identify a candidate compound of interest (e.g., using high throughput screening methods), for example, to treat a disease or disorder (e.g., schizophrenia including schizophrenia associated with 22q11 Deletion Syndrome, bipolar disorder, autism, diabetes or other disorders).

aPS cells according to the present invention also find use in regenerative medicine (see, e.g., US 2009/0155225 and US 2009/0220466 to Ratajczak et al.; and US 2010/0267107 to Zuba-Surma et al.).

The aPS cells for use according to the present invention can optionally be isolated and/or cultured according to the presented invention.

Having described the present invention, the same will be explained in greater detail in the following examples, which are included herein for illustration purposes only, and which are not intended to be limiting to the invention.

Example 1

Isolation of Stem Cells

In the example describe herein, 10 mL of peripheral blood was collected by routine venipuncture into sodium citrate (green top) tubes. If more blood is collected the processing steps are scaled up accordingly. The blood was kept at 37° C. in a water bath for less than 2 hours.

Contaminating red blood cells were removed by lysis by mixing 2.5 mL of whole blood with 47.5 mL of 37° C. hypotonic lysis buffer (BD Pharm, containing ammonium chloride, potassium carbonate, and EDTA) in a 50 mL centrifuge tube. Any other red blood cell lysis buffer may also be used. The tubes were gently vortexed for about 15 seconds, and then incubated in a 37° C. water bath protected from light for 15 minutes.

Alternatively, other body fluids and tissues can be obtained and processed as appropriate to that tissue using methods known to others familiar with the art.

The tubes were centrifuged at 1000 g for 30 minutes. The supernatant was decanted, and the pellet resuspended in phosphate buffered saline (PBS) (5 cm height). The cell suspension was centrifuged at 1000 g for 18 minutes. The supernatant was removed and the cells resuspended in PBS.

aPS cells are separated from the majority of other remaining cells in the peripheral blood by centrifugation over an isotonic density barrier medium. In this example, 500 uLs of isotonic PERCOLL™ with a specific gravity of 1.12 was placed in a 15 mL centrifuge tube. The cell suspension was carefully layered over the PERCOLL™. The height of the cell suspension was 10 cm.

Other density barrier materials, such as, but not limited to PERCOLL™ PERCOLL™ Plus, PURESPERM®, OPTIPREP™, FICOLL™, FICOLL-PAQUE™, FICOLL-PAQUE™ Plus, FICOLL-PAQUE™ Premium, NYCO-DENZ®, HISTOPAQUE™, an iodixanol solution, a sucrose solution, a cesium solution and/or a glycerol solution or any other suitable density barrier material may also be used. The specific gravity of the density barrier medium can optionally be at 1.1-1.12, although other specific gravities may be used. Alternative density based methods, such as a continuous flow cell separation method[30] may also be used.

The tube was centrifuged at 1000 g for 46 minutes, calculated using the aforementioned parameters and Stokes' Equation. To recover the aPS cells, the cell pellet above the PERCOLL™ was removed and discarded, and the cells below the PERCOLL™ were collected and resuspended in 5 mL of PBS (height is 5 cm). The cell suspension was centrifuged at 1000 g for 15 minutes.

The supernatant was removed. The cell pellet consists primarily of aPS cells; however, some red blood cells, platelets, and white blood cells may still contaminate the pellet. The contamination of the aPS pellet with other cells depends on the specific gravity chosen for the density barrier medium, and the care and skill of the technician to prevent contamination from the pellet above the density barrier medium.

Further purification of the aPS cells was achieved by negative immunomagnetic selection, using the MACS® cell separator system (Miltenyi Biotec). The cell pellet was labeled with antibody microbeads to CD45, CD61, and CD235a (Miltenyi Biotec) following the manufacturer's instructions. LD depletion columns were used with the midi magnet to remove contaminating cells, and the resulting eluate was collected in a 15 mL centrifuge tube.

Other immunomagnetic cell separation methods are known to those skilled in the art, and include DYNABEADS® (Dynal Biotech), EASYSEP™ (Stemcell Technologies), ROBOSEP™ (Stemcell Technologies), and the HG4100® Cell Separation system (Immunico). The Quadrasep QMS™ quadrupole magnetic sorter (Ikotech) and/or elutriation may also be used at this step.

The cell suspension was centrifuged at 1000 g for 20 minutes. The supernatant was removed. The cell pellet contained the isolated aPS cells.

Cells obtained with this method uniformly express OCT4, and vary from 1-4 microns in diameter (see FIG. 2).

Figure 3:
FIG. 3. aPS cells were isolated from 10 mL of whole blood from 3 healthy subjects with the density-based method as described in Example 1 herein. The aPS cell pellet was suspended in 70 μL of PBS, and the final volume of the cell suspension measured with a pipette. Cells were counted using a hemocytometer (Hausser Scientific); shown are cells in one 0.0625 mm² square (volume 6.25 nL). The image is viewed with an Olympus IX51 microscope at 20× and acquired with an Olympus DP12 camera. Arrows indicate live cells. In this example there are 17 cells identified in a volume of 6.25 nL, or 2.72 cells/nL. In the 70 μL cell suspension there were thus 190,400 aPS cells. Cell counts using this method are shown in FIG. 4.

To count the number of cells isolated we used two different methods. First, we counted cells using a hemocytometer (FIG. 3). Cells were resuspended in PBS and the exact volume of the cell suspension measured. The total number of cells isolated from 10 mL of whole blood was calculated for each subject (FIG. 4). Using this method we estimated that between 10,400-22,400 aPS cells/mL are isolated from whole blood.

An alternative method to count cells used flow cytometry. The method included fixing isolated cells with 4% paraformaldehyde, Fc blocking, labeling cells with PE labeled antibodies to SSEA4 (clone MC-813-70, Biolegend) and DRAQ5™ (Biostatus Limited). Cells were suspended in 450 µL of PBS, and then 50 µL of 5.2 micron calibration particles (Spherotech) are added. Cells and calibration particles were counted using a Becton Dickenson LSR II flow cytometer, and the relative number of SSEA4+ cells to calibration particles was used to calculate absolute number of cells (see FIG. 4).

Figure 5:
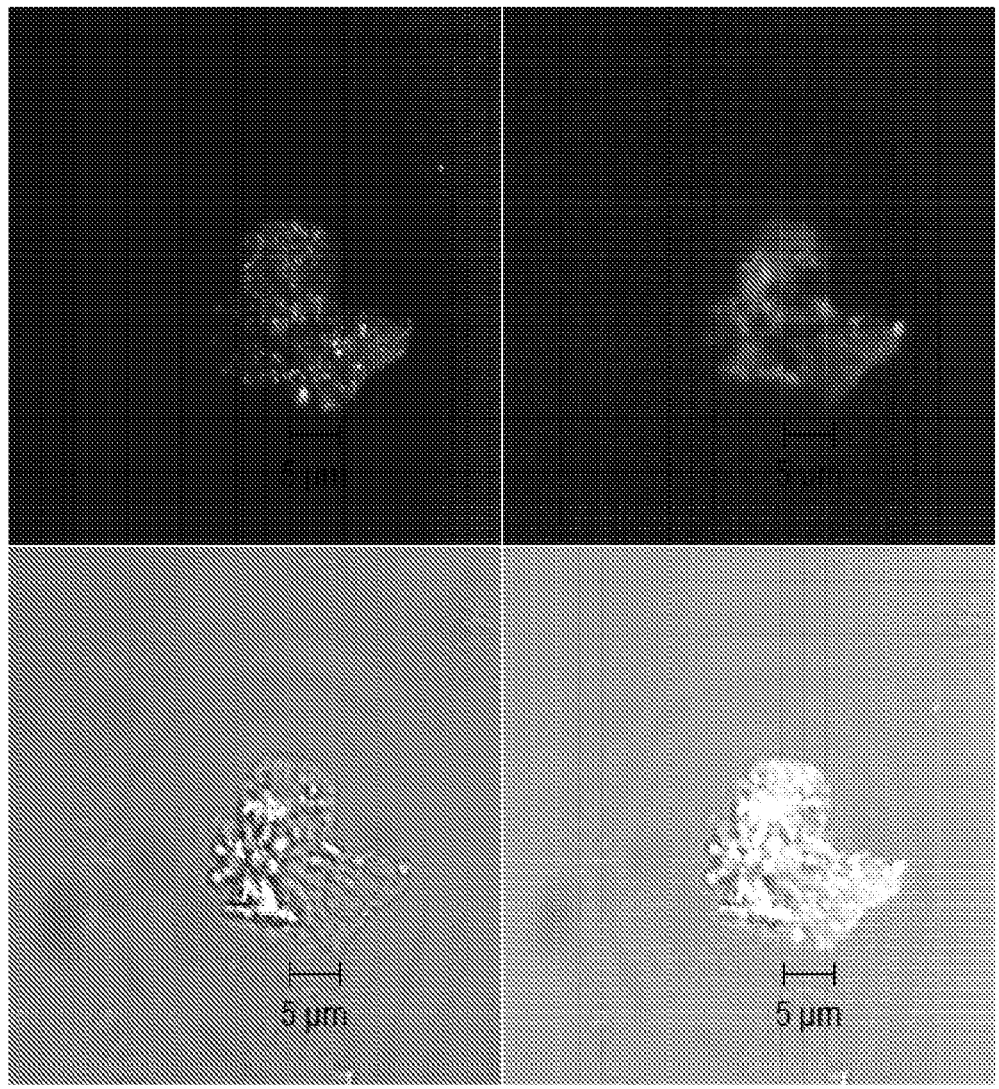
FIG. 5. aPS cells were isolated from 10 mL of whole blood from a healthy male with a density based method as described in Example 1 herein. Cells were fixed with 4% formaldehyde, were labeled in suspension with primary antibodies to OCT4 (polyclonal, Stemgent) (green; left panel) and SSEA4 (clone MC-813-70, Stemgent) (red; right panel), secondary antibodies were Northern Lights® (R&D Systems), washed, and then suspended in 70 μL of PBS. A 7 μL drop was plated on IMMUNOSELECT® Adhesion slides (Mo Bi Tec) and the slide placed in a moist chamber overnight to allow cells to adhere. The cells were mounted with Fluoro-Gel mounting medium (Electron Microscopy Sciences). A sealant (nail polish) was used to hold the cover slip in place. Images were obtained using a Zeiss 510 Laser Scanning Confocal Microscope at 63× oil objective by Dr. Neil Kramarcy in the UNC Michael Hooker Microscopy Facility.
Figure 6:
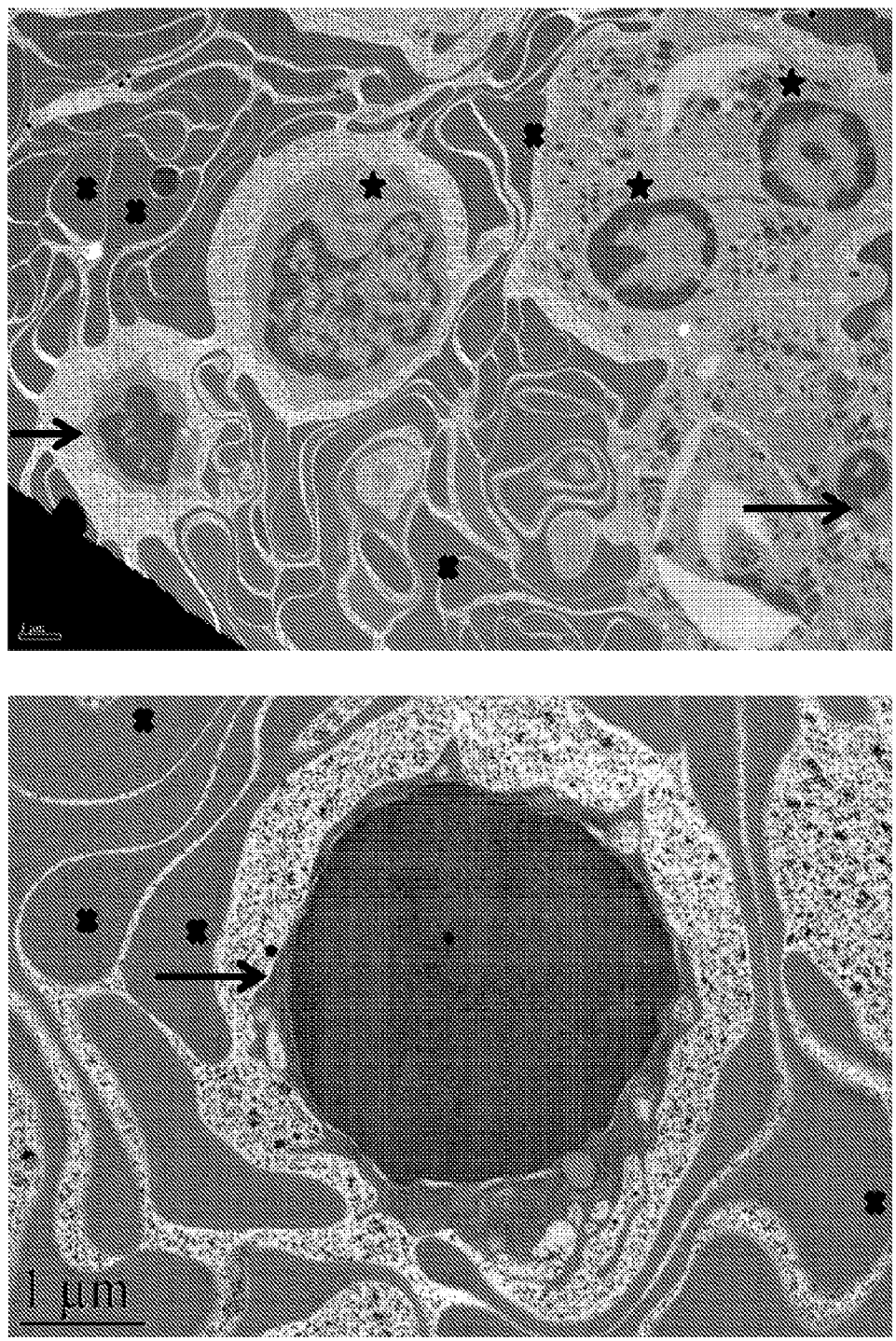
FIG. 6. Cells were pelleted from blood. Electron microscope images of three aPS cells, as indicate by black arrows. Note that the sizes of the cells range between 1-3 microns. The nucleus is characterized by dense heterochromatin. For comparison the larger cells indicated by a star are lymphocytes, and the more homogeneous cells are packed red blood cells.

Isolated aPS cells were characterized with immunocytochemistry methods (see FIG. 5). As observed under the light microscope with immunocytochemistry staining to mark platelets (CD61) and white blood cells (CD45), contaminating cells are rare and comprise less than 3% of the isolated cells. Isolated aPS cells were characterized with electron microscopy (FIG. 6). As observed a high magnification aPS cells are characterized by dense heterochromatin.

Figure 7:
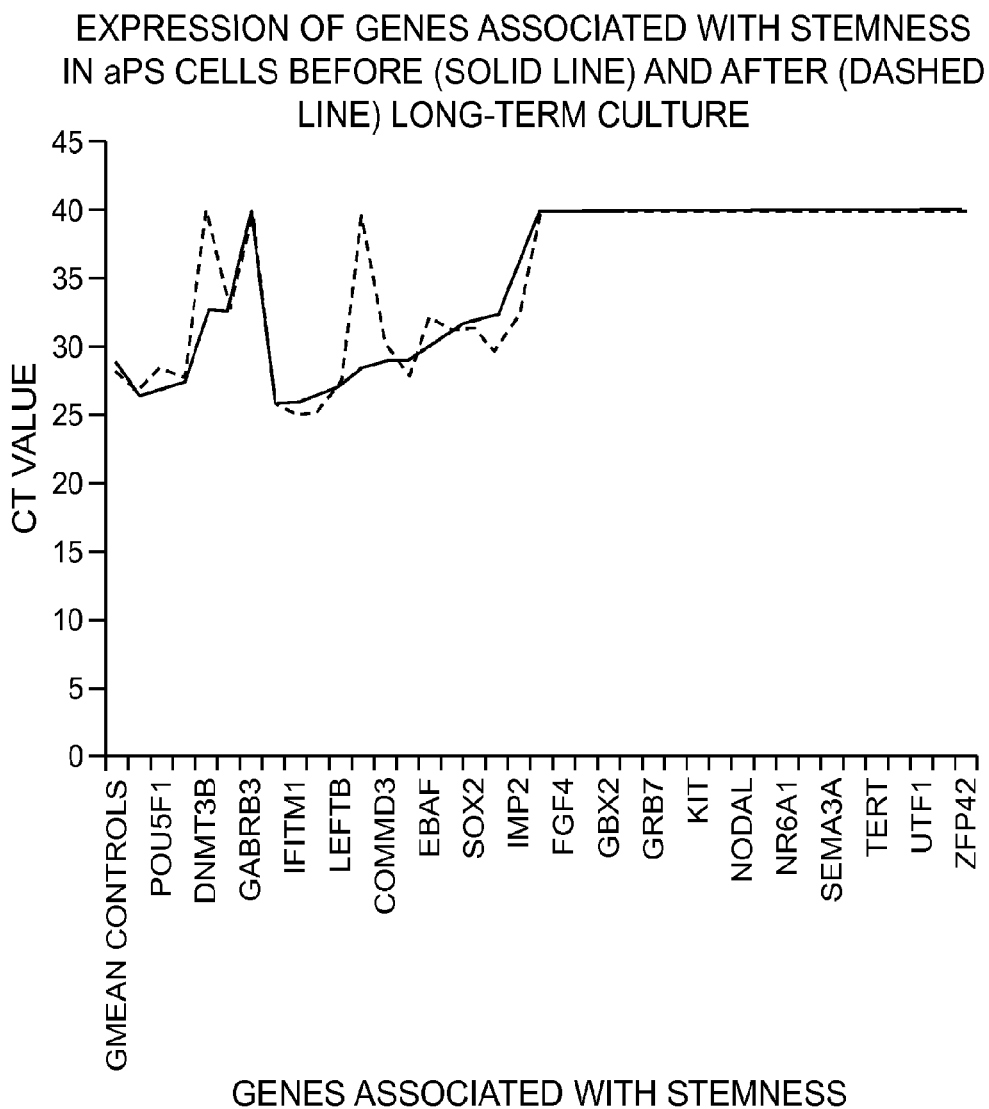
FIG. 7. Pluripotency gene expression was determined using a TaqMan® Stem Cell Pluripotency Array (Applied Biosystems). These assays for messenger RNAs (mRNAs) were performed according to the manufacturer's protocols. Control gene expression is the geometric mean of expression of EEF1A1, GAPD, 18S, CTNNB1, ACTB, and RAF1. Note that important genes indicating pluripotency are expressed at levels similar to housekeeping genes for both samples, including POU5F1 and NANOG. On culture DNMT3B and FGF5 expression emerge. Given the low amount of total RNA and the relatively low expression of control genes lack of gene expression of other pluripotency genes reported by others, especially TERT, may be related to inadequate total RNA to detect genes, rather than lack of expression.

We also characterized the isolated aPS cells based on the expression of pluripotency genes using a TAQMAN® Stem Cell Pluripotency Array (Applied Biosystems), according to manufacturer's instructions. Gene expression is shown in FIG. 7. As would be expected for a stem cell population, aPS cells express genes characteristic of pluripotent stem cells.

Example 2

Alternate Protocol for Isolating aPS Cells

As an alternative embodiment to isolate aPS cells from animal body fluids or tissues, a high throughput immunomagnetie separation method such as the Quadrasep QMC™ quadrupole magnetic sorter (Ikotech) may be used directly on whole blood, after lysis of red blood cells, or after density barrier separation.

In this embodiment, cells are labeled with appropriate antibodies against contaminating cell types, such as white blood cells, platelets, and red blood cells, or cells specific to the tissue used, but that will not substantially interact (or will not interact at all) with aPS cells. In embodiments, the antibodies also have small magnetic particles attached. The cell suspension is subject to a high throughput immunomagnetic separation method such as Quadrasep QMC™ quadrupole magnetic sorter (Ikotech) using methods known to those skilled in the art, and the appropriate fraction containing aPS cells is collected.

An alternative method uses positive selection for the aPS cells by labeling with antibodies against SSEA4, TRA-160, TRA-180, or CD326 or antibodies against other proteins characteristic, and optionally unique, to aPS cells.

An alternative embodiment includes positive selection based on immunomagnetic labeling of cells and immunomagnetic separation[28] or based on a microfluidics platform and antibody labeled microposts such as the CTC-Chip (modified to detect aPS-expressed antigens)[29]. For example, aPS cells are labeled with antibodies against an aPS cell expressed protein (optionally, an aPS cell specific protein), and then subject to high throughput microfluidics immunomagnetic separation, or a CTC-Chip is modified to have an appropriate antibody and the cell suspension is run through the chip, using methods known to those skilled in the art.

Example 3

Alternative Embodiment for Isolation of aPS Cells

In the example describe herein, 1 mL of peripheral blood was collected by routine venipuncture into sodium citrate (green top) tubes. If more blood is collected the processing steps can be scaled up accordingly. The blood was kept at 37° C. in a water bath for less than 2 hours.

In this example a sterile Ultrafree CL centrifuge filter tube fitted with a 5 micron filter is filled with 5.5 mL of PERCOLL™ with a specific gravity of 1.12 g/mL and briefly centrifuged so that the PERCOLL™ fills the outer tube and inner tube to the same level, and comes up to slightly above the filter of the inner tube. The 5 micron filter is large enough to allow passage of the aPS cells, and minimizes any mixing of the cell suspension with the density barrier material. One mL of whole blood is diluted with an equal volume of PBS, and the cell suspension was layered over the PERCOLL™ in the inner centrifuge tube, and the inner centrifuge tube was capped. The height of the cell suspension was 5 cm and the distance the cells needed to travel through the filter and the opening that communicates the contents of the inner and outer tubes and so to reach the outer tube was 1 cm. The tube was centrifuged at 1000 g for 90 minutes. The inner tube lid connecting it to the outer tube was cut, and the inner tube with contaminating cells was removed and discarded.

The contents of the outer tube, which contained the aPS cells, were transferred to a 15 ml centrifuge tube, and washed twice with PBS with centrifugation times calculated according to Stokes Equation. The supernatant was removed after each PBS wash. The cell pellet consists primarily of aPS cells; however, some cell debris and microvesicles still contaminate the isolated cells. A positive selection method was employed to separate cells from debris using SSEA4+ immunomagnetic beads (Dynabeads™). Immunomagnetic beads from other companies and alternative antibodies (e.g., TRA-1-60) may be substituted, or a negative selection as described in Example 1 may be employed.

Other density barrier materials, such as, but not limited to PERCOLL™, PERCOLL™ Plus, PURESPERM®, OPTIPREP™, FICOLL™, FICOLL-PAQUE™, FICOLL-PAQUE™ Plus, FICOLL-PAQUE™ Premium, NYCODENZ®, HISTOPAQUE™, an iodixanol solution, a sucrose solution, a cesium solution and/or a glycerol solution or any other suitable density barrier material may also be used. The specific gravity of the density barrier is optionally at 1.1-1.12, although other specific gravities may be used. Alternative density based methods, such as a continuous flow cell separation method[30] may also be used.

Alternatively, other body fluids and tissues can be obtained and processed as appropriate to that tissue using methods known to others skilled in the art.

Example 4

Expansion of Stem Cells

Isolated aPS cells were plated on a 48-well culture plate that was uncoated, as well as plates coated with Laminin 511 or MATRIGEL™. Cell culture medium was Euromed-N (Euroclone) supplemented with 1% N2 (Gibco) and 1% B27 (without retinoic acid, Gibco), EGF (20 ng/mL) and FGF2 (20 ng/mL). Cells were kept in a 37° C. incubator with 5% $CO_2$ and 5% $O_2$. Cell culture medium was changed every 2-3 days. Cells were passaged when the culture plate became about 80% confluent.

Figure 8:
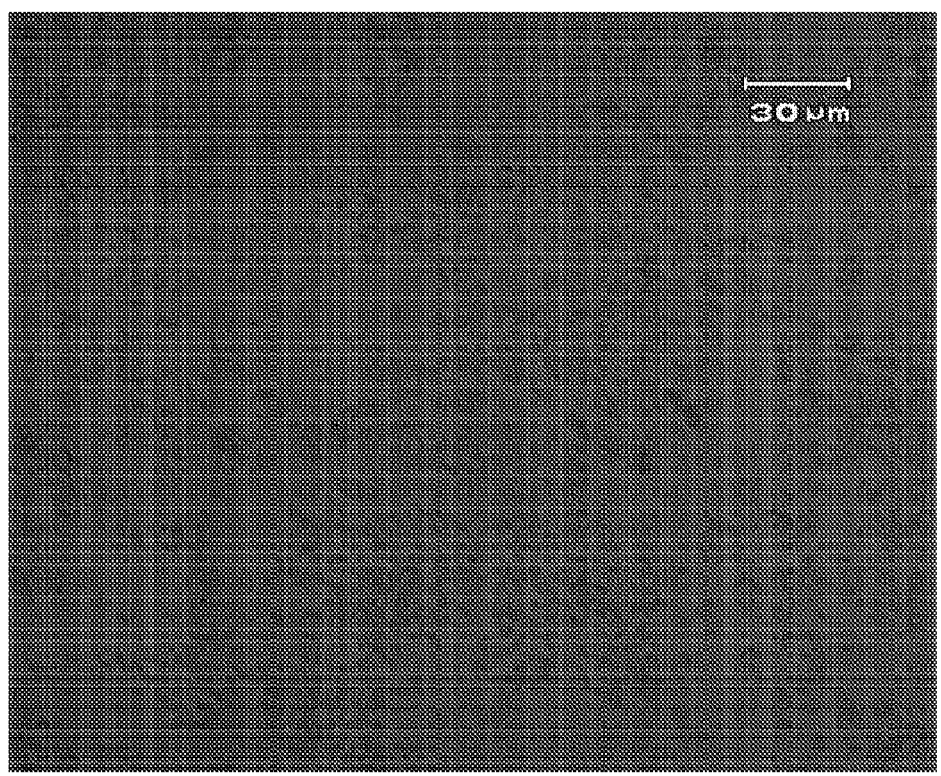
FIG. 8. Cells in continuous culture for one year on Laminin-511 coated plates in cell culture medium containing Euromed-N basal medium, insulin, transferrin, selenium, progesterone, putrescine, FGF2, and EGF. Cells form groups or exist as single cell, and range from 1-3 microns in size. Cells typically are motile when grown on plates. Phase contrast microscopy was performed with an Olympus IX51 microscope and images acquired with an Olympus DP12 camera. Images are viewed at 40×.
Figure 9:
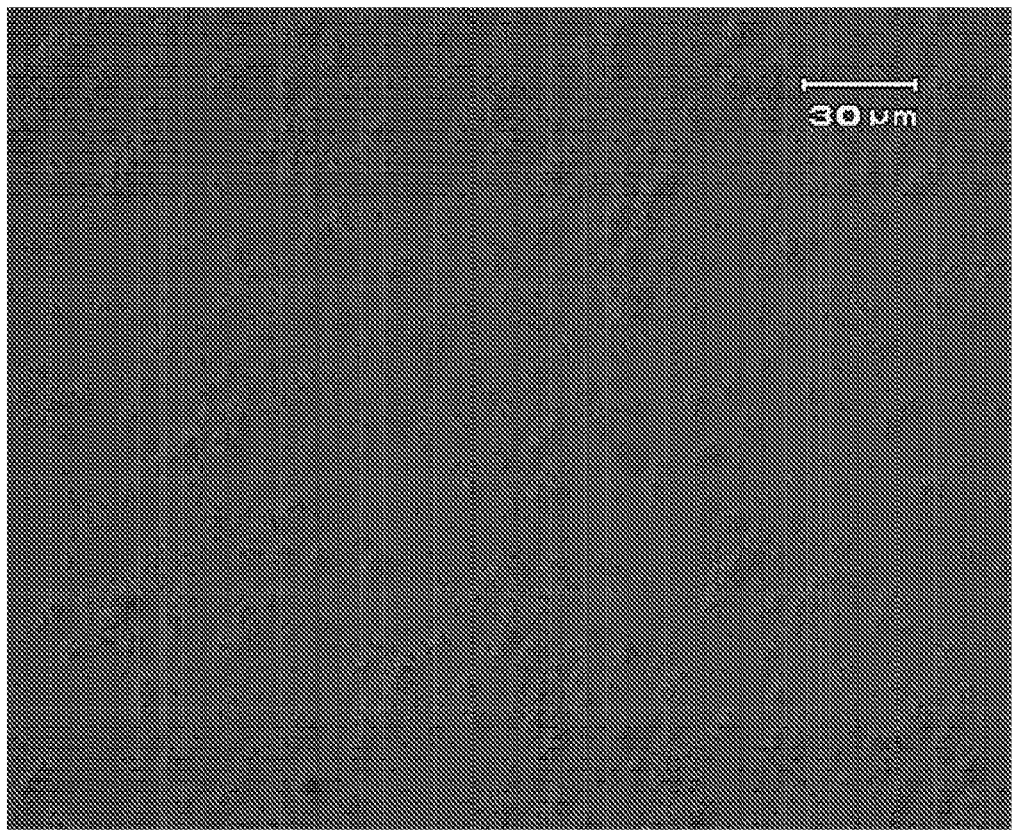
FIG. 9. Cells in continuous culture for one year on MATRIGEL® coated plate in cell culture medium containing Euromed-N, insulin, transferrin, selenium, progesterone, putrescine, FGF2, and EGF. Cells form groups or exist as single cell, and range from 1-3 microns in size. Cells typically are motile growing on plates. Phase contrast microscopy was performed with an Olympus IX51 microscope and images acquired with an Olympus DP12 camera. Images are viewed at 40×.

Cells cultured by this method have remained in continuous culture for over one year (see FIGS. 8 & 9).

Expression of pluripotency genes after 4 months in culture was determined using a TAQMAN® Stem Cell Pluripotency Array (Applied Biosystems). Gene expression is shown in FIG. 7.

Figure 10:
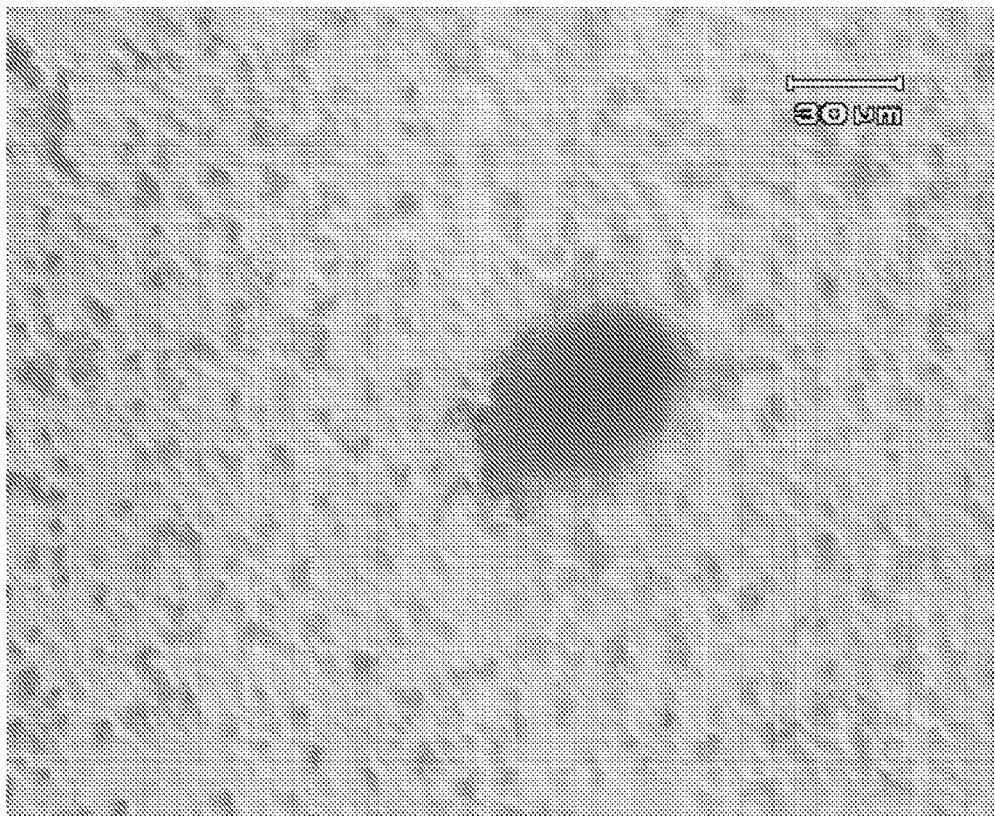
FIG. 10. Example of an embryoid body formed from aPS cells cultured for over one year. The cells were initially cultured in Euromed-N medium supplemented with N2, B27, L-glutamine, EGF and FGF2. Embryoid-like bodies formed when EGF and FGF2 were removed from the medium.
Figure 11:
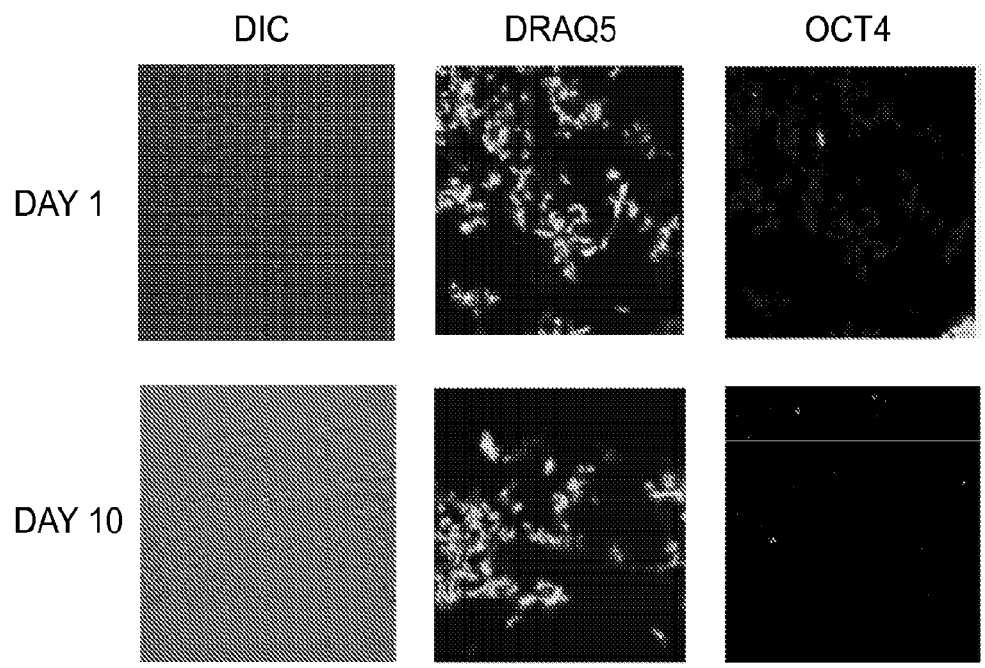
FIG. 11. Differentiation of aPS cells to neural stem cells, following the methods of Li and colleagues[10]. Cells lose expression of pluripotency protein OCT4, and gain expression of neural stem cell marker protein, PAX6. Images were obtained using a Zeiss 510 Laser Scanning Confocal Microscope at 40× oil objective.
Figure 11:
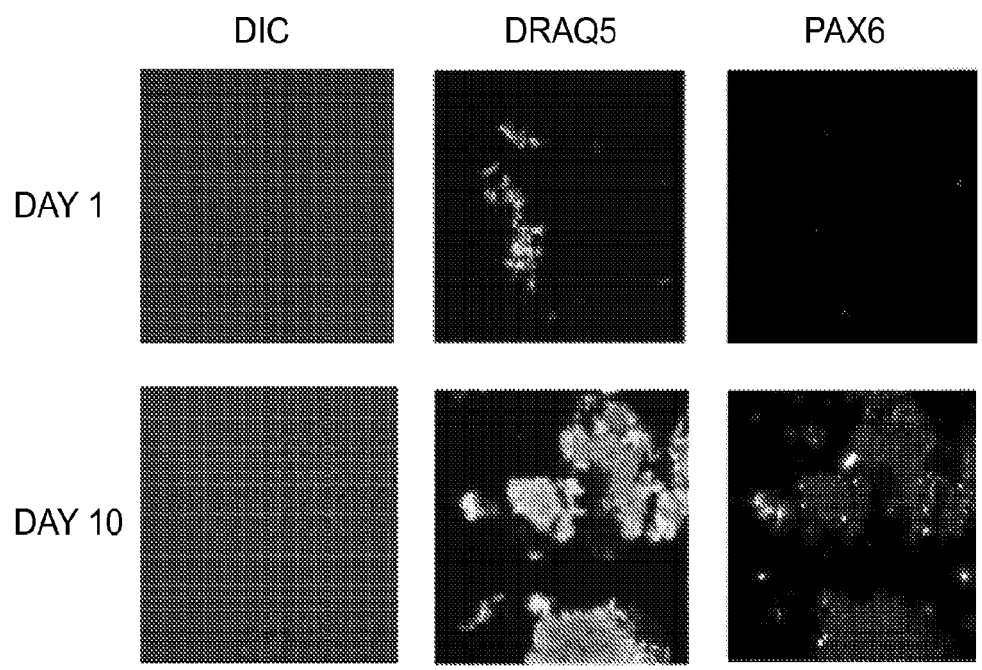

A variety of methods similar to those developed to induce differentiation of induced pluripotent stem cells are employed to induce differentiation of cultured aPS cells as desired. In this example, we withdrew mitogens from cells that had been in culture for over one year and observed embryoid-like body formation (FIG. 10). We also used a method described by Li and colleagues[10] to induce neural stem cell differentiation, as indicated by emergence of PAX6 expression and loss of OCT4 expression (FIG. 11).

Example 5

Alternative Embodiment for Expansion of Stem Cells

Isolated aPS cells were plated on a 96-well culture plate with an initial seeding of about 10,000 cells per well. Cell culture medium was DMEM/F12, supplemented with insulin (10 ng/mL), transferrin (5.5 ng/mL) and selenium (5 ng/mL), ascorbic acid 64 µg/mL, and either PDGF-AB (10 ng/mL) or FGF2 (100 ng/mL). Cells were kept in a 37° C. incubator with 5% $CO_2$ and 5% $O_2$. Cell culture medium was changed twice, on day 1 and day 7. Cells exhibited little expansion until week 6, and became confluent by week 8. Cells were able to continue to expand even after becoming confluent. Cells are maintained in this culture medium for 3 months with no change in phenotype.

Example 6

Use of Stem Cells aPS cells are used to evaluate safety and effectiveness of pharmaceuticals or other therapies for the prevention or treatment of an illness on an individualized basis, to determine disease mechanism on an individualized basis to yield individualized diagnosis, and/or to perform high-throughput screening of candidate drugs or treatments.

aPS cells are isolated using any method known in the art (e.g., the methods described herein) from persons with a disease of interest, for example a person with schizophrenia, bipolar disorder, autism, diabetes or other disorders. The isolated aPS cells can be cultured using any method known in the art, including the methods described herein.

In representative embodiments, a phenotype is determined that differentiates aPS cells isolated from a person with the disease from those of an unaffected person. Examples of the phenotype include, but are not limited to, cell migration, cell replication and/or expression of a gene or genes of interest. Phenotypes related to differentiated aPS cells include, but are not limited to, structural phenotypes (such as dendrite length in neurons), protein expression, DNA methylation status, gene-protein interactions, and/or RNA expression.

For example aPS cells isolated from persons with and without schizophrenia related to 22q11 Deletion Syndrome are used to determine molecular pathways involved in disease process on an individualized basis. The 22q11 Deletion Syndrome has a variable phenotype that includes congenital heart disease, defects in the palate, mild facial dysmorphias, immune system deficits, learning disabilities, and mental illness including schizophrenia. The reason for the variable phenotype related to 22q11 deletion syndrome is not known but could be related to differences in other genes that may moderate the impact of the 22q11 deletion.

aPS cell expression of mRNA and proteins from genes in the deleted region and other genes are measured using techniques known to those skilled in the art. Expression of other genes that are influenced by 22q11 genes, such as microRNA expression (related to the 22q11 gene DGCR8, a gene involved in microRNA biogenesis) are also measured. Gene expression is correlated to the phenotype of interest to determine what biological pathways mediate differences in phenotype, and thus determine disease mechanism on an individualized basis. In particular embodiments, gene expression is measured in undifferentiated aPS cells, or in aPS cells induced to differentiate along neuronal or immune lines.

Studies are carried out to determine if DGCR8 expression is low in aPS cells from 22q11 deletion syndrome patients as compared with persons without 22q11 deletion syndrome, to determine if DGCR8 levels correlate with microRNA expression, to determine if expression of DGCR8 and or microRNA levels are associated with a cell phenotype such as mitochondrial function, cell mobility, or cell replication rates, and, based on these findings, if replacement of DGCR8 corrects gene expression or other abnormal cell phenotypes.

A variety of small molecules, gene therapies, pharmaceuticals, or other treatments are applied to the aPS cells in culture to determine if the disease related phenotype is corrected. For example, if in 22q11 Deletion Syndrome patients the 22q11 deletion gene, DGCR8, is abnormally expressed, then gene replacement (for example application of DGCR8 mRNA or protein added to the cell using methods known to persons skilled in the art) is tested to determine if the cell phenotype is corrected. A nonlimiting example of a cell phenotype is the expression profile of several species of microRNA genes (a profile regulated in part by DGCR8). aPS cells induced to differentiate along neuronal lines may have abnormal neurite outgrowth patterns. It is determined whether DGCR8 gene replacement corrects the abnormal neurite outgrowth patterns. Such a strategy paves the way for the development of gene therapy with DGCR8 for persons with 22q11 Deletion Syndrome.

The foregoing is illustrative of the present invention, and is not to be taken as limiting thereof. The invention is defined by the following claims, with equivalents of the claims to be included therein.

REFERENCES

Chow, R. et al. Cell recovery comparison between plasma depletion/reduction- and red cell reduction-processing of umbilical cord blood. *Cytotherapy* 13, 1105-1119, doi: 10.3109/14653249.2011.592524 (2011).

Ratajczak, M. Z., Kucia, M., Ratajczak, J. & Zuba-Surma, E. K. A multi-instrumental approach to identify and purify very small embryonic like stem cells (VSELs) from adult tissues. *Micron* 40, 386-393 (2009).

Zuba-Surma, E. K. et al. Optimization of isolation and further characterization of umbilical-cord-blood-derived very, small embryonic/epiblast-like stem cells (VSELs). *Eur J Haematol* 84, 34-46, doi:EJH1352 [pii] 10.1111/j.1600-0609.2009.01352.x (2010).

Bhartiya, D. et al. Very small embryonic-like stem cells with maximum regenerative potential get discarded during cord blood banking and bone marrow processing for autologous stem cell therapy. *Stem cells and development* 21, 1-6, doi:10.1089/scd.2011.0311 (2012).

Henson, N. L. et al. Karyotypic analysis of adult pluripotent stem cells. *Histol Histopathol* 20, 769-784 (2005).

Bhartiya, D., Sriraman, K. & Parte, S. Stem cell interaction with somatic niche may hold the key to fertility restoration in cancer patients. *Obstet Gynecol Int* 2012, 921082, doi: 10.1155/2012/921082 (2012).

Ratajczak, M. Z., Zuba-Surma, E. K., Machalinski, B., Ratajczak, J. & Kucia, M. Very small embryonic-like (VSEL) stem cells: purification from adult organs, characterization, and biological significance. *Stem cell reviews* 4, 89-99 (2008).

McGuckin, C. et al. Embryonic-like stem cells from umbilical cord blood and potential for neural modeling. *Acta neurobiologiae experimentalis* 66, 321-329 (2006).

McGuckin, C., Jurga, M., Ali, H., Strbad, M. & Forraz, N. Culture of embryonic-like stem cells from human umbilical cord blood and onward differentiation to neural cells in vitro. Nature protocols 3, 1046-1055 (2008).

Li, W. et al. Rapid induction and long-term self-renewal of primitive neural precursors from human embryonic stem cells by small molecule inhibitors. *Proceedings of the*

*National Academy of Sciences of the United States of America* 108, 8299-8304, doi:1014041108 [pii] 10.1073/pnas.1014041108 (2011).

What is claimed is:

1. A method for isolating autologous pluripotent stem (aPS) cells from blood, the method comprising:
   (a) centrifuging the blood over a density barrier medium having a specific gravity of at least 1.09, such that a fraction containing the aPS cells migrates into the density barrier medium and to a position within and/or below the density barrier;
   (b) collecting the fraction within and/or below the density barrier medium containing the aPS cells; and
   (c)(i) applying negative selection using immunopurification, flow cytometry, elutriation and/or another continuous flow separation method to remove cells that are not aPS cells from the cell fraction collected in (b); and/or
   (c)(ii) applying positive selection to enrich the cell fraction collected in (b) for aPS cells using immunopurification, flow cytometry, elutriation and/or another continuous flow separation method.

2. The method of claim 1, wherein the aPS cells express POU5F1 (OCT4).

3. The method of claim 2, wherein the aPS cells express one or more other genes that characterize pluripotent stem cells.

4. The method of claim 1, wherein the aPS cells have a mean diameter in the range of 1 to 4 microns.

5. The method of claim 1, wherein the blood is treated to reduce the number of red blood cells prior to centrifugation in (a).

6. The method of claim 5, wherein a chemical agent is added to lyse red blood cells.

7. The method of claim 1, wherein centrifuging the blood animal cells in (a) comprises centrifuging the blood over a density barrier medium within an inner centrifuge tube, wherein the inner centrifuge tube comprises an opening formed in a bottom portion thereof and is positioned in an outer centrifuge tube, such that the density barrier medium is in communication between the inner and outer centrifuge tubes, and
   wherein there is a space between the bottom of the inner centrifuge tube and the bottom of the outer centrifuge tube, and
   wherein the inner centrifuge tube is enclosed; and
   wherein the blood is centrifuged such that the fraction containing the aPS cells migrates out of the inner centrifuge tube through the opening formed in the bottom portion thereof and into the density barrier medium to a position within and/or below the density barrier medium in the outer centrifuge tube.

8. The method of claim 7, wherein collecting the fraction in (b) comprises removing the inner centrifuge tube from the outer centrifuge tube, wherein the outer centrifuge tube comprises the fraction containing the aPS cells.

9. The method of claim 7, wherein the blood has not been treated to lyse and/or remove red blood cells.

10. The method of claim 9, wherein at least 90% of the red blood cells in the blood are retained within the inner centrifuge tube.

11. The method of claim 1, wherein the blood is centrifuged over the density barrier at a centrifugation force and duration calculated using Stokes' Equation.

12. The method of claim 1, wherein the blood is mammalian.

13. The method of claim 1, wherein the blood is human.

14. The method of claim 1, wherein the method further comprises culturing the aPS cells collected in (b).

* * * * *